(12) United States Patent
Scheiman et al.

(10) Patent No.: US 11,324,783 B2
(45) Date of Patent: May 10, 2022

(54) PROBIOTIC FORMULATIONS FOR IMPROVING ATHLETIC PERFORMANCE

(71) Applicant: President and Fellows of Harvard College, Cambridge, MA (US)

(72) Inventors: Jonathan Scheiman, Brighton, MA (US); George M. Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/395,588

(22) Filed: Aug. 6, 2021

(65) Prior Publication Data

US 2021/0369794 A1 Dec. 2, 2021

Related U.S. Application Data

(63) Continuation of application No. 16/092,080, filed as application No. PCT/US2017/026773 on Apr. 10, 2017, now Pat. No. 11,090,342.

(60) Provisional application No. 62/320,787, filed on Apr. 11, 2016.

(51) Int. Cl.
| | |
|---|---|
| *A61K 35/741* | (2015.01) |
| *A61K 35/748* | (2015.01) |
| *C12N 1/20* | (2006.01) |
| *A23L 33/135* | (2016.01) |
| *A23C 9/123* | (2006.01) |
| *A61K 35/744* | (2015.01) |
| *C12Q 1/02* | (2006.01) |
| *C12Q 1/689* | (2018.01) |
| *A61K 35/00* | (2006.01) |

(52) U.S. Cl.
CPC ............ *A61K 35/741* (2013.01); *A23C 9/123* (2013.01); *A23L 33/135* (2016.08); *A61K 35/744* (2013.01); *A61K 35/748* (2013.01); *C12N 1/20* (2013.01); *C12Q 1/025* (2013.01); *C12Q 1/689* (2013.01); *A23V 2002/00* (2013.01); *A61K 2035/115* (2013.01); *C12Q 2600/158* (2013.01)

(58) Field of Classification Search
CPC combination set(s) only.
See application file for complete search history.

(56) References Cited

U.S. PATENT DOCUMENTS

| | | | |
|---|---|---|---|
| 9,180,140 | B2 | 11/2015 | Lundberg et al. |
| 10,076,546 | B2 | 9/2018 | Henn et al. |
| 10,406,118 | B2 | 9/2019 | Lundberg et al. |
| 10,555,968 | B2 | 2/2020 | Lundberg et al. |
| 2007/0258953 | A1 | 11/2007 | Duncan et al. |
| 2010/0047344 | A1 | 2/2010 | Lundberg et al. |
| 2010/0092441 | A1 | 4/2010 | Lundberg et al. |
| 2012/0134973 | A1 | 5/2012 | Kekkonen |
| 2012/0178646 | A1 | 7/2012 | Spaink et al. |
| 2014/0112985 | A1 | 4/2014 | Bochenek et al. |
| 2015/0037285 | A1 | 2/2015 | Blaser et al. |
| 2015/0050320 | A1 | 2/2015 | Connell |
| 2015/0352147 | A1 | 12/2015 | Lundberg et al. |
| 2016/0030494 | A1 | 2/2016 | Henn et al. |
| 2018/0050070 | A1* | 2/2018 | Finlay ...................... C12N 1/20 |
| 2019/0125784 | A1 | 5/2019 | Lundberg et al. |
| 2019/0183924 | A1 | 6/2019 | Lundberg et al. |
| 2019/0192554 | A1 | 6/2019 | Lundberg et al. |

FOREIGN PATENT DOCUMENTS

| | | |
|---|---|---|
| WO | 2005105730 A2 | 11/2005 |
| WO | 2008105730 A1 | 9/2008 |
| WO | 2008105731 A1 | 9/2008 |
| WO | 2015/017625 A1 | 2/2015 |
| WO | 2015/164555 A1 | 10/2015 |
| WO | 2015/166492 A2 | 11/2015 |
| WO | 2016/141454 A1 | 9/2016 |

OTHER PUBLICATIONS

Clarke et al. "Exercise and associated dietary extremes impact on gut microbial diversity," Gut, Jun. 9, 2014 (Jun. 9, 2014), vol. 63, pp. 1913-1920. entire document.
Hsu et al. "Effect of intestinal microbiota on exercise performance in mice," J Strength Cond Res, Feb. 1, 2015 (Feb. 1, 2015), vol. 29, pp. 552-558. entire document.
Ohkuwa et al. "The Relationship between Exercise Intensity and Lactate Concentration on the Skin Surface," Int J Biomed Sci, Mar. 1, 2009 (Mar. 1, 2009), vol. 5, pp. 23-27. entire document.
Martarelli et al. "Effect of a Probiotic Intake on Oxidant and Antioxidant Parameters in Plasma of Athletes During Intense Exercise Training," Curr Microbiol, Mar. 12, 2011 (Mar. 12, 2011) vol. 62, pp. 1689-1696. entire document.
Martin et al. "Probiotic modulation of symbiotic gut microbial-host metabolic interactions in a humanized microbiome mouse model," Molecular Systems Biology, Jan. 15, 2008 (Jan. 15, 2008), vol. 4; Article No. 157, pp. 1-15. entire document.
Chen et al. "Food protein-based materials as nutraceutical delivery systems," Trends in Food Science & Technology. May 1, 2006 (May 1, 2006), vol. 17, pp. 272-283. entire document.
Extended European Search Report dated Nov. 20, 2019.
Scheiman et al. "Meta-omics analysis of elite athletes identifies a performance-enhancing microbe that functions via lactate metabolism" Nature Medicine, vol. 25; Jul. 2019; pp. 1104-1109.

* cited by examiner

*Primary Examiner* — Heidi Reese
(74) *Attorney, Agent, or Firm* — Banner & Witcoff, Ltd.

(57) ABSTRACT

A probiotic formulation is provided including one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

33 Claims, 15 Drawing Sheets

FIG. 5

| Taxon (Genus) | Taxon (Family) | Taxon (Phylum) | Comparison | Q-value |
|---|---|---|---|---|
| Faecalibacterium | Ruminococcaceae | Firmicutes | Higher in runners after marathon relative to runners pre-marathon | 0.02 |
| Faecalibacterium | Ruminococcaceae | Firmicutes | Higher in runners after marathon relative to sedentary controls | 0.02 |
| Oscillospira | Ruminococcaceae | Firmicutes | Higher in sedentary controls relative to marathon runners | 0.1 |
| Veillonella | Veillonellaceae | Firmicutes | Higher in runners after marathon relative to runners pre-marathon | 0.11 |
| Veillonella | Veillonellaceae | Firmicutes | Higher in runners after marathon relative to sedentary controls | 0.11 |
| Bacteroides | Bacteroidaceae | Bacteroidetes | Higher in sedentary controls relative to marathon runners | 0.11 |
| Dialister | Veillonellaceae | Firmicutes | Higher in runners before marathon relative to runners post-marathon | 0.11 |
| Dialister | Veillonellaceae | Firmicutes | Higher in runners before marathon relative to sedentary controls | 0.11 |
| N/A | N/A | Cyanobacteria | Higher in marathon runners relative to sedentary controls | 0.2 |
| N/A | Christensenellacea | Firmicutes | Higher in sedentary controls relative to marathon runners | 0.2 |
| Phascolarctobacterium | Veillonellaceae | Firmicutes | Higher in sedentary controls relative to marathon runners | 0.22 |
| Ruminococcus | Ruminococcaceae | Firmicutes | Higher in sedentary controls relative to marathon runners | 0.22 |
| Blautia | Lachnospiraceae | Firmicutes | Higher in sedentary controls relative to marathon runners | 0.22 |

US 11,324,783 B2

PROBIOTIC FORMULATIONS FOR IMPROVING ATHLETIC PERFORMANCE

RELATED APPLICATIONS

This application is a continuation application which claims priority to U.S. patent application Ser. No. 16/092,080 and filed Oct. 8, 2018; which is a National Stage Application under 35 U.S.C. 371 of PCT application PCT/US17/26773 designating the United States and filed Apr. 10, 2017; which claims the benefit of U.S. provisional application No. 62/320,787 and filed Apr. 11, 2016 each of which are hereby incorporated by reference in their entireties.

FIELD

The present invention relates in general to combinations, compositions and formulations including one or more of a probiotic for improving athletic performance.

BACKGROUND

Some 100 trillion microorganisms inhabit and colonize the human gut (Berg, R. D. "The indigenous gastrointestinal microflora." Trends Microbiol 4:430-5. 14 (1996); Young, V. B., and Schmidt, T. M. "Overview of the gastrointestinal microbiota." Adv. Exp. Med. Biol. 635:29-40 (2008)). These commensal organisms serve a wide range of functions increasingly recognized as mutualistic and indispensable for the health of the host, including proper digestion, metabolism, and importantly, colonization resistance against pathogens (Guarner, F. "Enteric flora in health and disease." Digestion 73 Suppl 1:5-12 (2006)).

Probiotic formulations exist as dietary supplements. Probiotics can be either resident or transient. Resident probiotic bacterial strains live and reproduce in each person's digestive tract. Transient probiotic bacterial strains typically are introduced into the body through ingested food or by means of dietary supplements. However, it would be desirable to create a probiotic formulation that is tailored to athletes to help improve athletic training, performance and recovery.

SUMMARY

The disclosure provides combinations, compositions and formulations including one or more of a probiotic. The probiotic improves athletic performance. The disclosure provides a probiotic formulation including one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria. The disclosure provides a method of altering bacterial species within a human including increasing population of the one or more bacteria, bacterial strains or bacterial species identified herein. The disclosure provides a method of supplementing bacterial species within a human before, during, or after physical activity including increasing population of one or more bacteria, bacterial strains or bacterial species identified herein. The disclosure provides a method of increasing or maintaining training endurance or performance endurance of a human including increasing population of one or more bacteria, bacterial strains or bacterial species identified herein. The disclosure provides a method of improving or maintaining athletic training, performance or recovery by a human during physical activity including increasing population of one or more bacteria, bacterial strains or bacterial species identified herein. The disclosure provides a method of recovering from physical activity resulting in inflammation and increased lactate levels comprising increasing a population of one or more bacteria, bacterial strains or bacterial species identified herein.

Further features and advantages of certain embodiments of the present invention will become more fully apparent in the following description of embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present embodiments will be more fully understood from the following detailed description of illustrative embodiments taken in conjunction with the accompanying drawings in which:

FIG. 5 is a summary of bacteria altered between study groups.

DETAILED DESCRIPTION

Figure 1A:
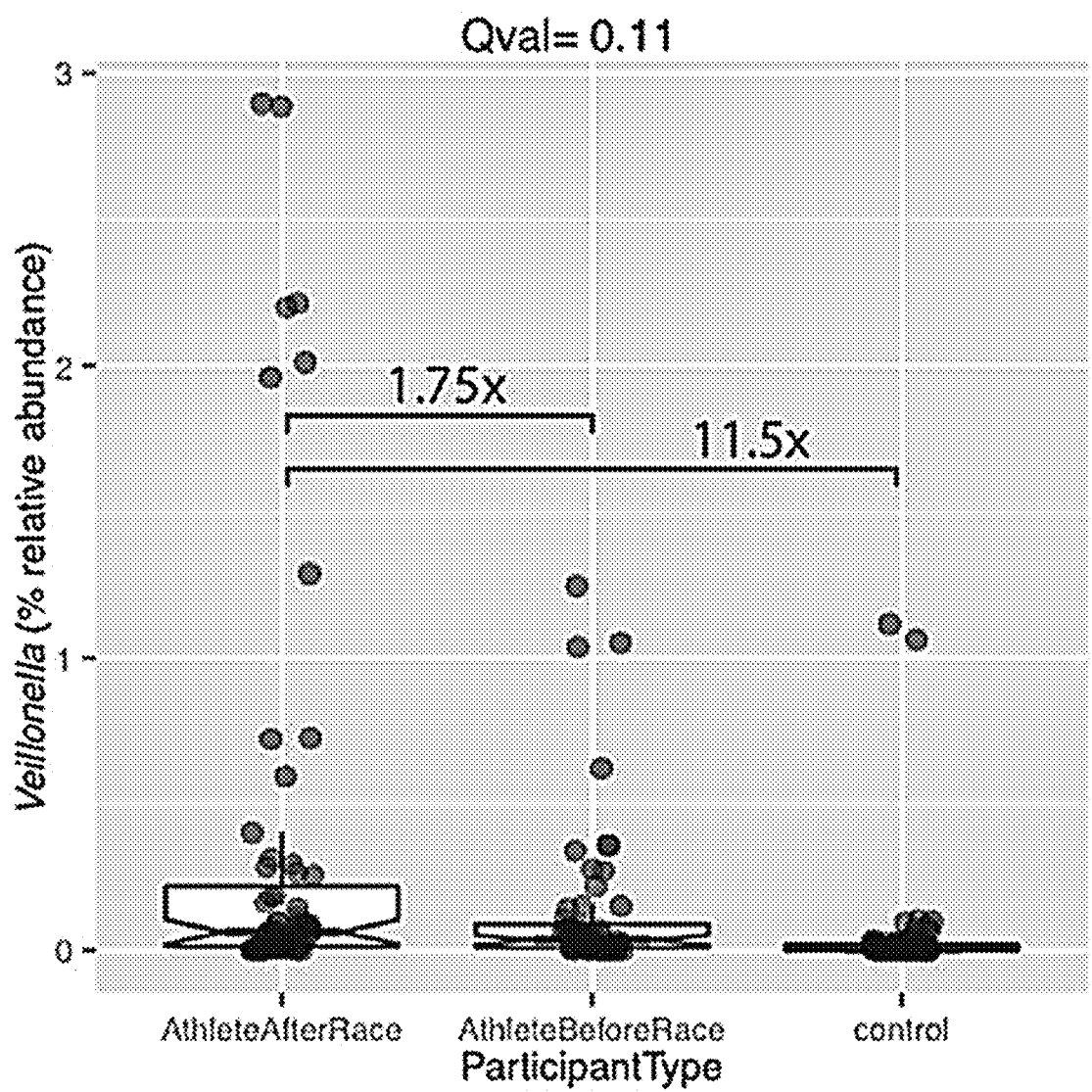
FIG. 1A depicts data demonstrating higher amount of *Veillonella* in an athlete after a race and before a race compared to a control.

The present disclosure provides combinations, compositions and formulations including one or more of a probiotic. The probiotic is one or more of a nonpathogenic bacterial phylum, family, genus, species or strain as identified herein as being included within the microbiome of an individual, such as an athlete. The probiotic is a mixture of two or more of a nonpathogenic bacterial phylum, family, genus, species or strain as identified herein as being included within the microbiome of an individual, such as an athlete. The disclosure provides administering an effective amount of the probiotic to the individual, such as an athlete. The disclosure provides administering an effective amount of the probiotic to the individual, such as an athlete, to alter one or more bacterial phylum, family, genus, species or strain within the individual. The disclosure provides administering an effective amount of the probiotic to the individual, such as an athlete, to supplement one or more bacterial phylum, family, genus, species or strain within the individual. The disclosure provides administering an effective amount of the probiotic to the individual, such as an athlete, to increase training endurance or performance endurance of the individual. The disclosure provides administering an effective amount of the probiotic to the individual, such as an athlete, to improve recovery of the individual during or after physical activity. The disclosure provides administering an effective amount of the probiotic to the individual, such as an athlete, to improve recovery of the individual during or after physical activity resulting in inflammation and increased lactate levels. The disclosure provides administering an effective amount of the probiotic to the individual, such as an athlete, to reduce lactate levels in the individual during or after physical activity generating increased lactate levels. The disclosure provides administering an effective amount of the probiotic to the individual, such as an athlete, to reduce inflammation in the individual during or after physical activity generating inflammation. The disclosure provides administering an effective amount of the probiotic to the individual, such as an athlete, to increase energy metabolism in the individual during physical activity. The disclosure provides administering an effective amount of the probiotic to the individual, such as an athlete, to promote weight loss or fitness.

The disclosure provides a combination of one or more or all of the bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria in a formulation. For example, the disclosure provides a formulation to include all of a bacteria, bacterial strain or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, and phylum cyanobacteria, or any subset combination thereof.

Probiotics are dead or live non-toxic microbial food supplements that can beneficially affect a host by improving the host's gut or intestinal microbial balance, composition and/or functionality without causing disease. The disclosure provides determination of an exemplary microbiome of an athlete and a non-athlete. The disclosure provides comparison of the exemplary microbiome of an athlete and a non-athlete. The disclosure provides identification of bacterial phylum, family, genus, species or strain that is increased or decreased as a result of physical activity. The disclosure provides identification of a probiotic formulation including one or more bacterial phylum, family, genus, species or strain that are increased or decreased as a result of physical activity.

The term "athlete" may refer to a person who is proficient in sports and other forms of physical exercise or a person who is trained or skilled in exercises, sports, or games requiring physical strength, agility, endurance, speed or stamina or a person who possesses above average physical skills such as strength, agility, endurance, speed or stamina and is suited for physical competition.

The term "physical exercise" may refer to any bodily activity that enhances or maintains physical fitness and overall health and wellness. It is performed for various reasons, including strengthening muscles and the cardiovascular system, honing athletic ability or skills, weight loss or maintenance, and merely enjoyment.

"Increasing or maintaining training endurance or performance endurance" refers to a comparison of training endurance or performance endurance using objective factors for a particular individual. Such objective factors may include ability to continue a particular exercise or training event over a given period of time. Such exercises or training events are known to those of skill in the art and can be determined based on the particular athletic event or sport engaged in by the individual.

"Improving or maintaining athletic training, performance or recovery" refers to a comparison of athletic training, performance or recovery using objective factors for a particular individual. Such objective factors may include ability to continue a particular exercise or training event over a given period of time. Such exercises or training events are known to those of skill in the art and can be determined based on the particular athletic event or sport engaged in by the individual. Such objective recovery factors include the length of time it takes for an individual to perform at the same or similar level between an athletic event, training, performance or physical activity.

Probiotic Compositions or Formulations Information from one or more of the following disclosures as is known to those of skill in the art and as described herein may be useful in the practice of the present disclosure: 2015/0351442, 2015/0335577, 2015/0305385, 2015/0290261, 2015/0246081, 2015/0203378, 2015/0071890, 2014/0356329, 2014/0324454, 2014/0242050, 2014/0242034, 2013/0295226, 2013/0280225, 2013/0273155, 2013/0273016.

Probiotic organisms, in general do not permanently colonize the body because of alteration antibiotic treatments, for example. Probiotics are intended as a supplement and are generally ingested regularly for effects to be maintained or persist. After ingestion, probiotics typically adhere to a tissue of the host, such as the wall of the intestine or gut or other tissue. Once attached, the desirable bacteria are capable of multiplying and colonizing, thereby enhancing optimal microflora balance. They are used to promote healthy microflora balance in the lower GI tract and healthy pH balance (yeast fungus) in the oral cavity, large intestine and vaginal tract and minimize microbial imbalance or dysbiosis. Certain probiotics can have, but are not limited to, the following characteristics: (1) from human origin; (2) stable and viable, gastric and bile acid resistant; (3) effectively adhere to and colonizing at the site of action; (4) compete with pathogens for adhesion sites; and (5) produce pathogen inhibitory substances, e.g. bacteriocidins and organic acids.

Probiotics are sometimes combined with prebiotics (where the combination may be referred to as "symbiotic") which include one or more non-digestible dietary supplements, which modify the balance of the intestinal micro flora, stimulating the growth and/or activity of beneficial microorganisms and suppressing potentially deleterious microorganisms. Exemplary supplements include oligosaccharides (fructo-oligosaccharides, galacto-oligosaccharides); Inulin, Lactulose, Lactitol and select bacterial strains that produce nutrients that promote the growth of beneficial bacteria, such as within the intestinal tract. The disclosure provides that prebiotics promote within an individual the proliferation of one or more of the bacterial phylum, family, genus, species or strain as identified herein as being included within the microbiome of an individual, such as an athlete.

The term "nonpathogenic" is intended to mean a microbial species for which no pathology of the host associated with its presence has been demonstrated (strain GRAS=Generally Recognized As Safe).

The terms "microorganism" or "microbe" in certain instances may refer to an organism of microscopic size, to a single-celled organism, and/or to any virus particle. The definition of microorganism used herein includes Bacteria, Archaea, single-celled Eukaryotes (protozoa, fungi, and ciliates), and viral agents.

The term "microbial" in certain instances may refer to processes or compositions of microorganisms, thus a "microbial-based product" is a composition that includes microorganisms, cellular components of the microorganisms, and/or metabolites produced by the microorganisms. Microorganisms can exist in various states and occur in vegetative, dormant, or spore states. Microorganisms can also occur as either motile or non-motile, and may be found as planktonic cells (unattached), substrate affixed cells, cells within colonies, or cells within a biofilm.

The term "prebiotic" in certain instances may refer to food ingredients or bacterial producing ingredients that are not readily digestible by endogenous host enzymes and confer beneficial effects on an organism that consumes them by selectively stimulating the growth and/or activity of a limited range of beneficial microorganisms, such as those that are associated with the intestinal tract. Also the term includes one or more live microorganisms that confer beneficial effects on a host organism. Benefits derived from the establishment of probiotic microorganisms within the digestive tract include reduction of pathogen load, improved microbial fermentation patterns, improved nutrient absorption, improved immune function, improved intestinal hormonal signaling and metabolic regulation, aided digestion, increasing training endurance or performance endurance, reducing lactate levels in a human during or after physical activity generating increased lactate levels, reducing inflammation within a human resulting from physical activity, increasing energy metabolism within a human during physical activity, improving athletic training, performance or recovery by a human during physical activity, recovering from physical activity resulting in inflammation and increased lactate levels, or promoting weight loss or fitness.

The term "Symbiotic" in certain instances may refer to a composition that contains both probiotics and prebiotics. Symbiotic compositions are those in which the prebiotic compound selectively favors the probiotic microorganism.

The disclosure provides a probiotic composition or formulation including at least one phylum, family, genus, species or strain of bacteria, preferably from 1 to 30, and more preferably from about 10 to 25 different phylum, family, genus, species or strain of bacteria. The phylum, family, genus, species or strain of bacteria is generally present in a pre-determined location within the gastrointestinal tract of a subject and preferably the pre-determined location is the ileum or colon or gut. It is to be understood that the species of bacteria may be different or just include different strains of the same species.

The probiotic formulation comprises a mixture of bacterial genera that is reflective of the mixture of strains derived from the ileum of an individual, such as a healthy individual, such as an athlete. An exemplary probiotic includes the number of organisms being provided, administered or released is more than $10^6$ and less than $10^{12}$. Preferably, the providing, administration or release of the organisms of the probiotic formulation is in the distal segments of the gastrointestinal tract including the ileum and colon of a subject. An effective probiotic formulation comprises a live bacterial suspension including one or more of the following bacterial species: genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

Making Probiotic Compositions or Formulations

One or more bacterial organisms, such as one or more of genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria may be mixed together by conventional methods to form a composition or formulation and formed into an ingestible liquid medium, a gel medium, a food stuff, a food product, a freeze dried product or powder, a yogurt, a pill, a tablet, a capsule, a gelatin capsule, a caplet, a chewable formulation, a dissolvable formulation and the like, such as for oral administration. The disclosure provides a probiotic composition or formulation that may also contain conventional food supplement fillers and extenders such as, for example, a flour, a binder, a neutraceutical compound or formulation, a prebiotic, an amino acid, a vitamin, or a mineral.

The disclosure provides that the one or more probiotic bacterial organisms may be microencapsulated to provide a release profile that targets replacement or revision of one or more species of live bacteria at a pre-determined location within the gastrointestinal tract of a mammal. Such microencapsulation formulations and techniques may protect the live probiotic organisms from the digestive actions of the stomach, duodenum, and jejunum of the intestine and allow administration, delivery or release to the gut or ileum of an individual. Microencapsulated live probiotic organisms and formulations thereof are provided herein in various dosage forms, and they can be co-administered with drugs, foods, nutrients, vitamins, other beneficial substances, prebiotics, and other therapeutic agents such as pH encapsulated glucose, lipids or proteins that release in the distal small intestine at pH values between 7.0 and 8.0 in an amount sufficient to alleviate said disorder in a subject. Preferably, at least two coating are used to cover a tablet or capsule like form comprising the probiotic organism, wherein the outside coating is degraded in a pH environment of 5 to 6 and the inside coating is degraded in a pH environment of about 7 thereby dropping the probiotics in the ileum area and in close proximity to the Peyer's Patches. An exemplary coating may include one or more of poly(dl-lactide-co-glycolide, chitosan, casein, chitosan (Chi) stabilized with PVA (polyvinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization, The disclosure provides for a probiotic composition that may be referred to, for example, as a nutritional composition or as a pharmaceutical composition. A nutritional composition may include the probiotic composition and may be consumed in any form, such as a food product. A pharmaceutical composition may include the probiotic composition in combination with a pharmaceutically acceptable carrier which may include one or more excipients. Pharmaceutically acceptable carriers or excipients are well known in the pharmaceutical art, and are described, for example, in Remington's Pharmaceutical Sciences, Mack Publishing Co. (A. R. Gennaro edit. 1985). For example, saline and phosphate-buffered saline at physiological pH may be used. Stabilizers, dyes and even flavoring agents may be provided in the nutritional or pharmaceutical compositions describe herein.

The disclosure provides for a probiotic composition that may be administered orally, in the form of capsules, tablets, powders, granules, solutions, or suspensions. The at least one bacterial phylum, family, genus, species or strain can be mixed with conventional excipients, such as gelatin, starch, lactose, magnesium stearate, talc, gum arabic and the like. It may also be advantageous to use less conventional excipients that, for example, make it possible to increase the ability of the at least one bacterial phylum, family, genus, species or strain used to be active in the gut. For example, cellobiose, maltose, mannose, salicine, trehalose, amygdalin, arabinose, melobiose, rhamnose and/or xylose may be added. This list is not exhaustive and the substrates are chosen and adapted as a function of the phylum, family, genus, species or strain considered.

The probiotic composition or formulation may be combined with a drug, acetaminophen, foods, nutrients, vitamins, beneficial substances, prebiotics, pH encapsulated glucose, lipids or proteins that release in combination with the probiotics or in a pH of from about 1 to 6 and before the release of the probiotics. Also the probiotic formulation may also be co-administered with an antibiotic selected from the group consisting of vancomycin, metronidazole, gentamicin, colistin, fidaxomicin, telavancin, oritavancin, dalbavancin and daptomycin.

The disclosure provides a probiotic composition that may include a substrate that may promote growth of the at least one phylum, family, genus, species or strain present in the composition. Thus, the composition may include at least one additive which promotes the activity of the at least one strain in the digestive environment.

The disclosure provides a kit including one or more phylum, family, genus, species or strain of bacteria described herein, which may be in composition or formulation or encapsulated form, or powder, or pill or tablet or capsule and the like and may be provided within a container, and with a device for measuring units of the composition or formulation and with instructions for administration of the composition or formulation to an individual, such as an athlete.

Suitable dosages of a probiotic composition or formulation may be provided orally at a dosage rate of about 100 milligrams to 800 milligrams per day. Preferably, the dosage rate, effective as a food supplement and for reestablishing beneficial bacteria in the intestinal tract is between about 200 to 400 milligrams per day.

Bacterial strains useful according to the subject invention may be obtained commercially and/or produced by a fermentation process and, optionally, drying. The phylum, family, genus, species or strain may be grown on a suitable medium, under conditions of strict anaerobiosis, in the presence of a carbon-based substrate and/or a carbon based energy source; the bacterial cells are recovered; the bacterial cells are packaged. The bacterial cells may be recovered by centrifugation, for example between 10,000 g and 15,000 g, advantageously 12,000 g, for 15 to 20 minutes. The bacterial cells may be washed in, for example, an anaerobic phosphate buffer, by resuspension of the cells, agitation, and a further centrifugation step.

The disclosure provides that the one or more phylum, family, genus, species or strain of bacteria described herein may be in a dried form. The drying of bacterial strains after production by fermentation is known to those of skill in the art and includes EP 0 818 529 hereby incorporated by reference in its entirety, where a drying process of pulverization is described. Additional methods are described in WO 0144440, which is also incorporated by reference in its entirety. Bacterial microorganisms described herein are concentrated from a medium and dried by spray drying, fluidized bed drying, lyophilization (freeze drying) or other drying process. Micro-organisms can be mixed, for example, with a carrier material such as a carbohydrate such as sucrose, lactose or maltodextrin, a lipid or a protein, for example milk powder during or before the drying.

The disclosure provides that the phylum, family, genus, species or strain of bacteria described herein need not necessarily be present in a dried form. It may also be suitable to mix the bacteria directly after fermentation with a food product and, optionally, perform a drying process thereafter. Such an approach is disclosed in PCT/EP02/01504) which is incorporated by reference in its entirety. Likewise, a probiotic composition as described herein may also be consumed directly after fermentation. Further processing, for example, for the sake of the manufacture of convenient food products, is not a precondition for the beneficial properties of the bacterial strains provided in the probiotic composition.

The disclosure provides for the consumption of a probiotic composition described herein in the form of a fermented, dairy product, such as a chilled dairy product, a yogurt, or a fresh cheese. If the bacterial strain is added to a nutritional formula, the skilled person is aware of the possibilities to achieve this. Dried, for example, spray dried bacteria, such as obtainable by the process disclosed in EP 0 818 529 (which is incorporated herein by reference in its entirety) may be added directly to a nutritional formula in powdered form or to any other food product. For example, a powdered preparation of the bacterial strain(s) of the invention may be added to a nutritional formula, breakfast cereals, salads, a slice of bread prior to consumption.

The probiotic composition described herein may be added to a liquid product, for example, a beverage or a drink. If it is intended to consume the bacteria in an actively-growing state, the liquid product comprising the bacterial strain(s) should be consumed relatively quickly upon addition of the bacteria. However, if the bacteria are added to a shelf-stable product, quick consumption may not be necessary, so long as the bacterial strain(s) are stable in the beverage or the drink.

The probiotic composition described herein may be dried with a food product as described in WO 98/10666, which is incorporated herein by reference in its entirety. Accordingly, the subject bacterial strain(s) may be dried at the same time with juices, milk-based products or vegetable milks, for example, yielding a dried product already comprising probiotics. This product may later be reconstituted with an aqueous liquid.

Although it is not mandatory, probiotic bacteria may be consumed in the living state with the intention that the probiotic micro-organisms arrive intactly in the small and large intestines the latter of which may be colonized. If this is the case, a sufficient dose of bacteria is usually consumed per day in order to achieve successful colonization. The skilled person is aware of daily doses, which depend on the micro-organisms but generally are in the range of $10^6$ to $10^{14}$, or $10^7$ to $10^{13}$ cfu per day. Suitable dosage amounts for probiotic organisms may, for example, vary from about $10^5$ to $10^{12}$ organisms, typically about $10^6$ based on the numbers of organisms found in the ileum of the individual. Similarly, delivery of compounds provided herein will be specific to particular cells, conditions, and locations, such as ileum. In general, dosage is from tablets, capsules, granules and microgranules, powders, liquids and alike, and which may be given in single or multiple doses, once or more daily, weekly, monthly or yearly, or even less frequently.

The disclosure provides that dead or living probiotics, their medium, substrate or metabolites may be directly added to food products in the same or a similar way as set forth above for living probiotics more specifically. The fermented medium, substrate or metabolites may be separated from the bacteria after fermentation by centrifugation or filtration, for example. The supernatant or the filtrate may then be concentrated, chilled, frozen, dried, for example, spray dried or directly used for enteral administration to an individual. If fermented medium is dried, it may be powdered and, as described above for the living bacterial strain(s), added to any food product.

The disclosure provides methods of identifying bacterial phylum/genus/species/strains as probiotics and/or diagnostics for sports performance and recovery, for example for use by athletes. Such probiotics increase training endurance or performance endurance, reduce lactate levels during or after physical activity generating increased lactate levels, reduce inflammation resulting from physical activity, increase energy metabolism during physical activity, improve athletic training, performance or recovery during physical activity, improve recovery from physical activity resulting in inflammation and increased lactate levels, promoting weight loss or fitness, improve activity of the xenobiotic metabolism pathway or that improve the starch and sucrose metabolism pathway. The disclosure provides a method of modulating bacterial phylum/genus/species/strains for optimizing sports performance and recovery, such as for example by using food, prebiotics, small molecules, etc. that promote the microbiome of the athlete. The disclosure provides for the use of animals for personalized performance and recovery models, such as by transplanting athlete microbiomes into germ free mice and then screening recipient animals with diets, supplements, prebiotics, small molecules, etc. (and combinations thereof) for promotion of optimal microbiome composition.

The disclosure provides for the identification of bacteria significantly altered in abundance or activity, within athletes and/or distinct from sedentary controls, for use as either a performance biomarker or to be delivered as a probiotic to aid athletic performance and recovery, including being altered or provided or increased through administration of food products and supplements, prebiotics, and/or small molecules. The disclosure provides methods of altering metabolic pathways that are altered within athletes and/or distinct from controls by the administration of bacteria as a probiotic. The disclosure provides methods of identifying or otherwise determining which bacterial species can serve as performance and recovery probiotics or which can be altered through food, supplements, prebiotics, and/or small molecules. The disclosure provides methods of improving athlete performance by increasing lactate threshold, and thus preventing fatigue, by utilizing lactate fermenting bacteria as a probiotic from the genus *Viellonella, Oscilospira*, and *Ruminococcus*—independently or in combination as well as in conjunction with lactate producing probiotics, such as *lactobacillus*. The disclosure provides methods of improving recovery from inflammation in athletes after performance/exercise by utilizing bacteria as a probiotic from the genus' *Dialister, Phascolarctobacterium, Bacteroides, Faecalibacterium*, and *Blautia*—either independently or in combination.

The disclosure provides a probiotic formulation including one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria. The disclosure provides that the probiotic formulation includes bacteria of the genus *Veillonella* and genus *Faecalibacterium*. The disclosure provides that the probiotic formulation includes bacteria of the genus *Phascolarctobacteria*, genus *Oscillospira*, genus *Ruminococcus*, genus *Bacteroides*, genus *Blautia*, and family Christensenellaceae. The disclosure provides that the probiotic formulation includes bacteria of the genus *Veillonella*, genus *Faecalibacterium*, genus *Dialister*, and phylum cyanobacteria. The disclosure provides that the probiotic formulation includes bacteria of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, and phylum cyanobacteria. The disclosure provides that each of the one or more bacterial species of the probiotic formulation are present in the formulation in an equal amount by weight. The disclosure provides that each of the one or more bacterial species of the probiotic formulation are present in the formulation in an amount of between about 10 to about 90 weight percent to achieve a total weight percent of 100. The disclosure provides that the one or more bacterial species of the probiotic are live bacteria or dead bacteria. The disclosure provides that the probiotic formulation further includes a prebiotic, an amino acid, a vitamin, or a mineral. The disclosure provides that the probiotic formulation is in an ingestible liquid medium. The disclosure provides that the probiotic formulation is in a food stuff or food product. The disclosure provides that the probiotic formulation is in the form of a freeze dried powder. The disclosure provides that the probiotic formulation is in a yogurt. The disclosure provides that the probiotic formulation is in a pill or tablet. The disclosure provides that the probiotic formulation is in a chewable formulation. The disclosure provides that the probiotic formulation is in a dissolvable formulation. The disclosure provides that the probiotic formulation includes one or more neutraceutical compounds. The disclosure provides that the probiotic formulation includes the one or more bacterial species in an amount sufficient to increase the population of the one or more bacterial species within an individual.

The disclosure provides a method of altering one or more bacteria, bacterial strains or bacterial species within a human by increasing population of one or more bacteria, bacterial strains or bacterial species from the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria. The disclosure provides that the one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria are administered to the human. The disclosure provides that one or more prebiotics are administered to the human which increase the population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

The disclosure provides a method of supplementing bacteria, bacterial strains or bacterial species within a human before, during, or after physical activity by increasing population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria. The disclosure provides that the one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria are administered to the human. The disclosure provides that one or more prebiotics are administered to the human which increase the population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

The disclosure provides a method of increasing or maintaining training endurance or performance endurance of a human by increasing population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria. The disclosure provides that the one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria are administered to the human. The disclosure provides that one or more prebiotics are administered to the human which increase the population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

The disclosure provides a method of reducing lactate levels in a human during or after physical activity generating increased lactate levels by increasing within the human one or more bacteria, bacterial strains or bacterial species of the genus *Veillonella*, genus *Oscillospira*, or genus *Ruminococcus*. The disclosure provides that the one or more bacteria, bacterial strains or bacterial species of the genus *Veillonella*, genus *Oscillospira*, or genus *Ruminococcus* are administered to the human. The disclosure provides that one or more prebiotics are administered to the human which increase the population of one or more bacteria, bacterial strains or bacterial species of the genus *Veillonella*, genus *Oscillospira*, or genus *Ruminococcus*.

The disclosure provides a method of reducing inflammation within a human resulting from physical activity by increasing within the human one or more bacteria, bacterial strains or bacterial species of the genus *Faecalibacterium*, genus *Phascolarctobacteria*, genus *Bacteroides*, genus *Blautia* or genus *Dialister*. The disclosure provides that the one or more bacteria, bacterial strains or bacterial species of the genus *Faecalibacterium*, genus *Phascolarctobacteria*, genus *Bacteroides*, genus *Blautia* or genus *Dialister* are administered to the human. The disclosure provides that one or more prebiotics are administered to the human which increase the population of one or more bacteria, bacterial strains or bacterial species of the genus *Faecalibacterium*, genus *Phascolarctobacteria*, genus *Bacteroides*, genus *Blautia* or genus *Dialister*.

The disclosure provides a method of increasing energy metabolism within a human during physical activity by administering to the human the phylum cyanobacteria.

The disclosure provides a method of improving or maintaining athletic training, performance or recovery by a human during physical activity by increasing population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria. The disclosure provides that the one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria are administered to the human. The disclosure provides that one or more prebiotics are administered to the human which increase the population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

The disclosure provides a method of recovering from physical activity resulting in inflammation and increased lactate levels by increasing a population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria within a human. The disclosure provides that the one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria are administered to the human. The disclosure provides that one or more prebiotics are administered to the human which increase the population of one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria.

The disclosure provides a method of promoting weight loss or fitness by a human by increasing a population of bacteria, bacterial strains or bacterial species from the family Christensenellaceae within the human. The disclosure provides that the bacteria, bacterial strains or bacterial species of the family Christensenellaceae is administered to the human. The disclosure provides that a prebiotic is administered to the human which increases the population of one or more bacteria, bacterial strains or bacterial species of the family Christensenellaceae.

The disclosure provides an animal model including one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria which represent the microbiome of an athlete.

The disclosure provides a method of screening a compound that modulates the microbiome of an athlete by administering a test compound to an animal including one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, or phylum cyanobacteria, and determining the level of the one or more bacteria, bacterial strains or bacterial species of the genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, and phylum cyanobacteria. The disclosure provides that the test compound is present in a food, a beverage or a supplement.

The disclosure provides a method of supplementing the microbiome of an athlete after exercise by administering one or more bacteria, bacterial strains or bacterial species that improve activity of the xenobiotic metabolism pathway of the athlete.

The disclosure provides a method of supplementing the microbiome of an athlete after exercise by administering one or more bacteria, bacterial strains or bacterial species that improve the starch and sucrose metabolism pathway of the athlete.

The disclosure provides a method of determining bacterial species either uniquely associated with, altered in abundance within, or altered in activity within a first individual with a regular exercise regimen compared to a control individual without a regular exercise regimen including sequencing a first fecal sample from the first individual to identity the bacterial species present and active in the first fecal sample, sequencing a control fecal sample from the control individual to identity the bacterial species present and active in the control fecal sample, and comparing the bacterial species present and active in the first fecal sample to the bacterial species present and active in the control fecal sample to identify bacterial species increased or decreased in the first fecal sample compared to the control fecal sample. The disclosure provides that the bacterial species altered in activity is determined by altered RNA expression or altered metabolite expression. The disclosure provides that the identified bacterial species are candidate probiotics for administration to an athlete to improve training, performance or recovery. The disclosure provides that the identified bacterial species are candidate biomarkers of athletic training, athletic performance or recovery from physical activity resulting in inflammation and increased lactate levels. The disclosure provides that the identified bacterial species are candidate biomarkers of personalized nutrition.

The terms and expressions that have been employed are used as terms of description and not of limitation, and there is no intent in the use of such terms and expressions to exclude any equivalent of the features reported and described or portions thereof, but it is recognized that various modifications are possible within the scope of the invention as claimed. Thus, it will be understood that although the present disclosure includes preferred embodiments and optional features, modification and variation of the concepts herein disclosed may be resorted to by those skilled in the art, and that such modifications and variations are considered to be within the scope of the appended claims.

The following examples are set forth as being representative of the present disclosure. These examples are not to be construed as limiting the scope of the present disclosure as these and other equivalent embodiments will be apparent in view of the present disclosure, figures and accompanying claims.

Example I

Experimental Design

To identify bacteria associated with athletic performance and recovery states, participants running the 2015 Boston marathon were recruited to provide fecal samples on a daily basis up to one week before and one week after the event. To identify bacteria that are either enriched or diminished specifically in athletes, control sedentary participants—who identified as not regularly exercising, were also recruited to provide samples for up to two weeks for comparison.

Methods

Fecal Sample Collection

Study participants collected their own samples in private by dipping the wide end of a 1 ml pipette tip into fecal material, placing into a 15 ml falcon tube, and then storing at 4° C. until time of pickup—which ranged from the day of to 2 days after collection. Samples were placed at −80° C. for long term storage.

16s Library Preparation

For microbial DNA extraction, fecal samples were thawed on ice and then resuspended and vortexed in 1-5 mls of phosphate buffered saline. 250 ul aliquots of each sample were added to MO BIO Power Soil htp 96 well DNA extraction plates (MOBIO), following the kit protocol, and DNA was eluted into 50 ul of nuclease free water. For bacterial identification, next generation sequencing libraries were generated in a two-step PCR amplification protocol, using the hot start Q5 high fidelity DNA polymerase following protocol cycling conditions (NEB). First, 1-10 ul of extracted DNA from each sample was amplified using primers that flank variable region 4 of the 16S ribosomal DNA (rDNA) loci. 1 ul of this 16S rDNA PCR product was then used to amplify and attach illumina sequencing adaptors and barcodes. Amplified libraries were cleaned and concentrated with ZR-96 well plates (Zymogen) and then quantified initially by Quant-iT PicoGreen (Invitrogen), followed by KAPA universal library quantification kit (KAPA Biosystems). Equal molar ratios of each 16S library were pooled together and then sequenced on an Illumina miSeq.

Computational Methods: Raw 16S Sequence Analysis

All raw 16S sequence analysis was performed using the QIIME suite of tools as described in Caporaso, J. G., Kuczynski, J., Stombaugh, J., Bittinger, K., Bushman, F. D., Costello, E. K., et al. (2010). QIIME allows analysis of high-throughput community sequencing data. *Nature methods*, 7(5), 335-336 hereby incorporated by reference in its entirety, version MacQIIME 1.9.1-20150604 (world wide website wernerlab.org/software/macqiime), except where noted. All steps were performed with the standard parameters and databases associated with this version of MacQIIME except where noted. Paired end sequencing reads were converted from FASTQ to FASTA format and joined on their 3' segments using the 'join_paired_ends.py' QIIME script. Closed reference operational taxonomic units (OTUs) were selected from the resulting joined reads using the 'pick_closed_reference_otus.py' QIIME script and reference database that is bundled with this version of MacQIIME. The resulting table consisting of raw read counts will be referred to as the "OTU Table." Taxonomies were summarized from the cumulative relative abundances OTUs on each level of the tree (i.e. Phylum, Class, Order, Family, Genus, and Species) using the 'summarize_taxa.py' QIIME script, and then these tables were merged using the 'merge_otu_tables.py' QIIME script. This table consisting of relative abundances will be referred to as the "Taxonomy Table."

Computational Methods: Alpha Diversity Calculations

Alpha diversity was measured on the OTU Table first by rarefying at an even depth of 15,000 reads per sample using the 'multiple_rarefactions_even_depth.py' QIIME script then the 'alpha_diversity.py' QIIME script using the following alpha-diversity metrics: ace, berger_parker_d, brillouin_d, chao1, chao1_ci, dominance, observed_otus, shannon, simpson, and simpson_e.

Computational Methods: Beta Diversity Calculations

Beta diversity analysis was performed on the OTU Table using the 'jackknifed_beta_diversity.py' QIIME script and a rarefaction value of 7,000 reads per sample, producing both weighted and unweighted UniFrac distances across the dataset.

Computational Methods: PICRUSt Analysis

Functional metagenomic analysis on the 16S dataset was performed by PICRUSt analysis on the OTU Table. The OTU abundances were normalized for 16S copy number using the 'normalize_by_copy_number.py' PICRUSt script followed by metagenome prediction with the 'predict_metagenomes.py' script. The gene functions were then organized hierarchically according to KEGG (world wide website genome.jp/kegg/) orthology hierarchies.

Computational Methods: Linear Mixed Effect Model for Feature Association

Linear Mixed Effect Model for Feature Association is a statistical framework applied to datasets derived from both OTU and PICRUSt analysis, both referred to as the "feature matrix" with samples in rows and features in columns. The R Markdown script "Kostic_FeatureAssociation_01.Rmd", can be opened in a text file reader. The feature matrix is pre-normalized to make it compositional (i.e. each row sums to 1). The data is then filtered to remove features with the lowest variance. The feature matrix is matched against the metadata file (i.e. "mapping file") sample-by-sample, and then each metadata variable is tested independently for inclusion into the linear mixed effect (LME) model using the 'Maaslin' R package. For all features that correlate with metadata variables of interest, a plot is produced and assessed by eye to determine the strength of the correlation.

Example II

Figure 1B:
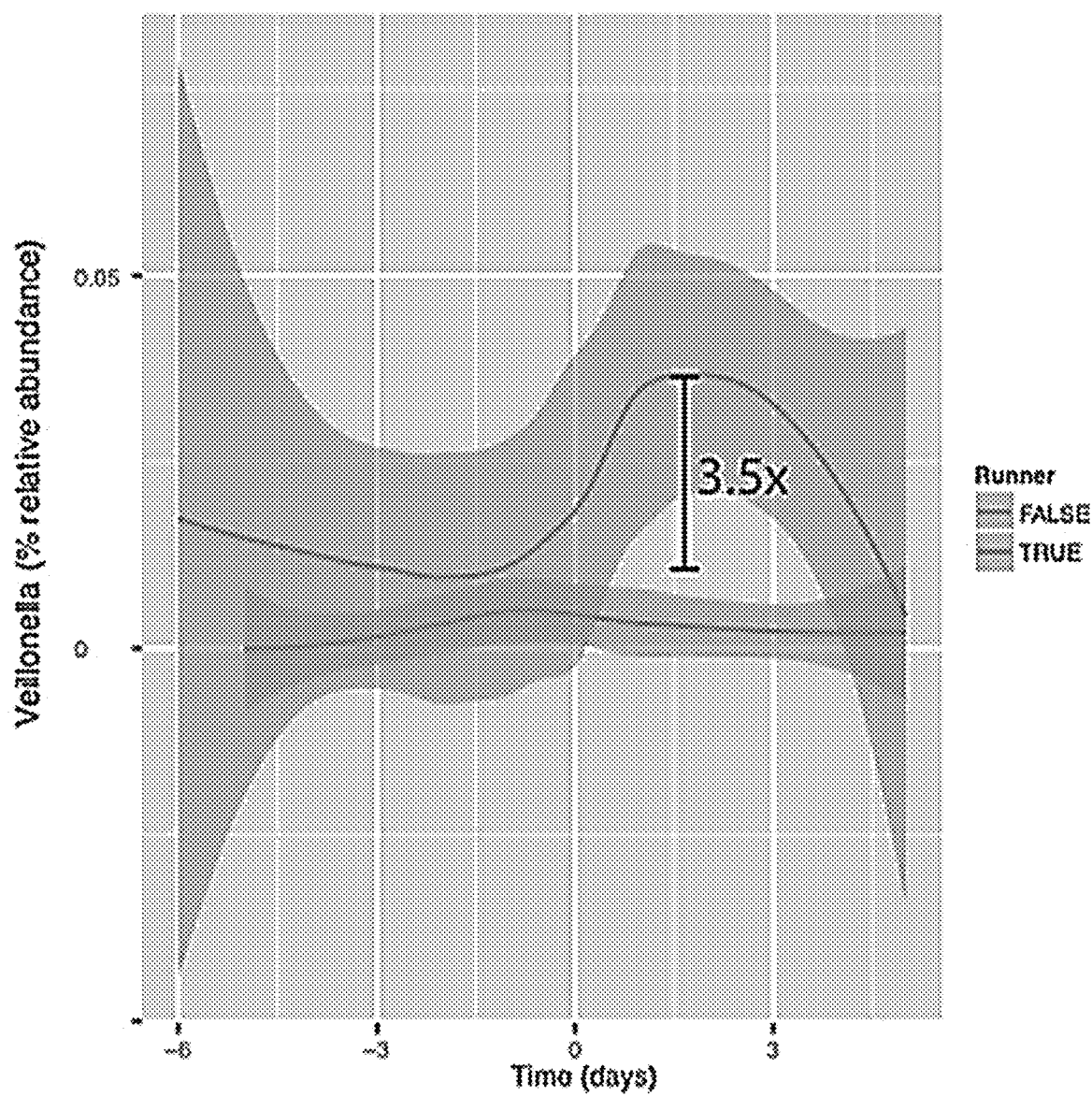
FIG. 1B depicts *Veillonella* abundance in an athlete one day after running a race.

The following bacteria was identified in an athlete as being significantly elevated in abundance after running a marathon: Family: Veillonellaceae; Genus: *Veillonella*. Averages of 16S sequences, grouped by study participant type (sedentary controls, athletes before race, and athletes after race) show approximately a 12 fold increase in abundance of the *Veillonella* genus between athletes after running the marathon and controls (FIG. 1A). Additionally, on average, there is approximately a 2 fold increase in *Veillonella* abundance in athletes after the race as compared to before (FIG. 1A). Longitudinal analysis of microbial composition in athletes show a spike in *Veillonella* abundance approximately one day after running the marathon (3.5 fold above pre-marathon levels), which returns to levels similar to that of controls, approximately four days after the marathon (FIG. 1B). Species in this genus grow on and ferment lactate (lactic acid). Lactate is a byproduct of anaerobic energy production in muscles under intense exercise and build up has been shown to cause the burning sensation during intense physical activity which leads to muscle fatigue and tightness. The disclosure provides that increased *Veillonella* abundance in athletes, particularly after the marathon, indicates an increase in lactate levels, and relates to a microbial response to clearing excess lactate through fermentation. The disclosure provides a method of increasing *Veillonella* abundance to reduce lactate and improve endurance for extended intense exercise, by preventing lactate buildup.

Example III

Figure 1C:
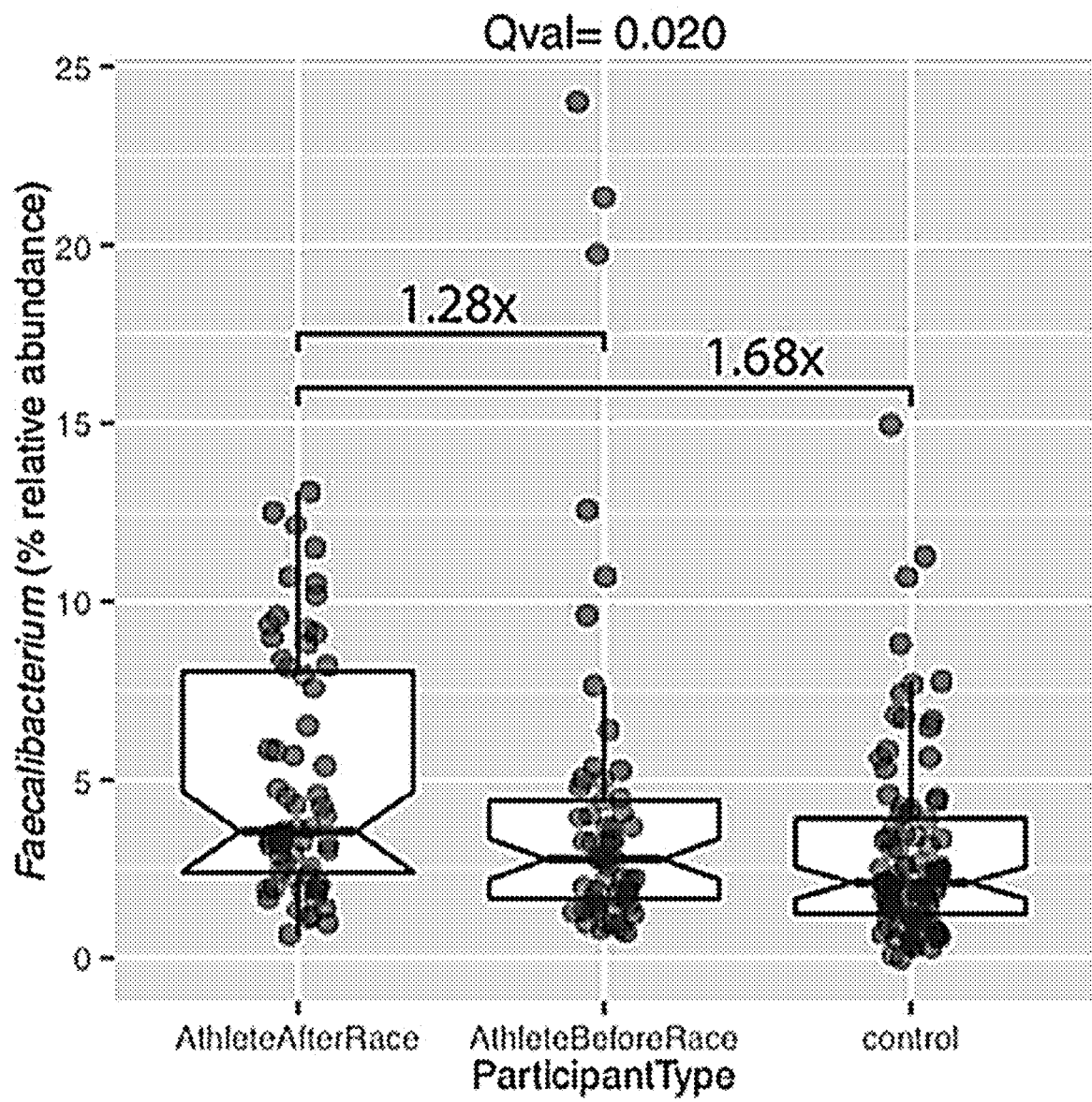
FIG. 1C depicts data demonstrating higher amount of *Faecalibacterium* in an athlete after a race and before a race compared to a control.

The following bacteria was identified in an athlete as being significantly elevated in abundance after running a marathon: Family: Ruminococcaceae; Genus: *Faecalibacterium*. Averages of 16S sequences, grouped by study participant type, show approximately a 2 fold increase in *Faecalibacterium* abundance in athletes after the marathon as compared to controls (FIG. 1C). Higher levels of *Faecalibacterium* are associated with health and anti-inflammation. The disclosure provides a method of increasing *Faecalibacterium* abundance in athletes to reduce inflammation and improve recovery.

Example IV

Figure 2A:
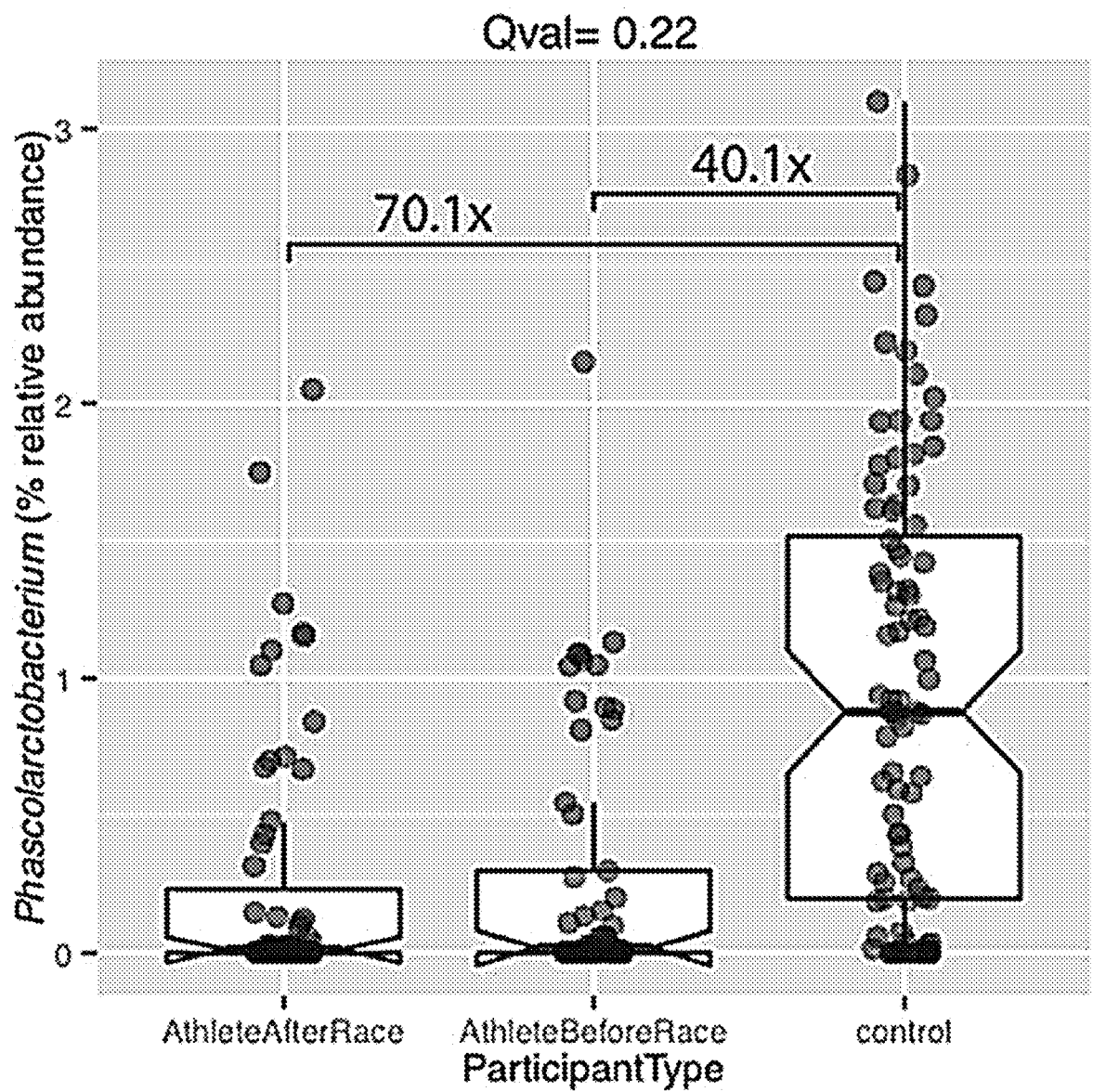
FIG. 2A depicts data demonstrating lower amount of *Phascolarctobacteria* in an athlete after a race and before a race compared to a control.

The following bacteria was identified in an athlete as being significantly reduced in abundance after running a marathon: Family: Veillonellaceae; Genus: *Phascolarctobacteria*. Averages of 16S sequences, grouped by study participant type, show a 40 fold increase in *Phascolarctobacteria* abundance for controls as compared to athletes before the race, and a 70 fold increase in abundance compared to athletes after the race (FIG. 2A). Decreased levels of *Phascolarctobacteria* has been associated with inflammatory bowel disease, indicating a potential for anti-inflammatory functions. Therefore, lower levels of *Phascolarctobacteria* in athletes, especially after running the marathon, may indicate higher inflammation levels. The disclosure provides a method of increasing *Phascolarctobacteria* abundance in athletes to reduce inflammation and improve recovery.

Example V

Figure 2B:
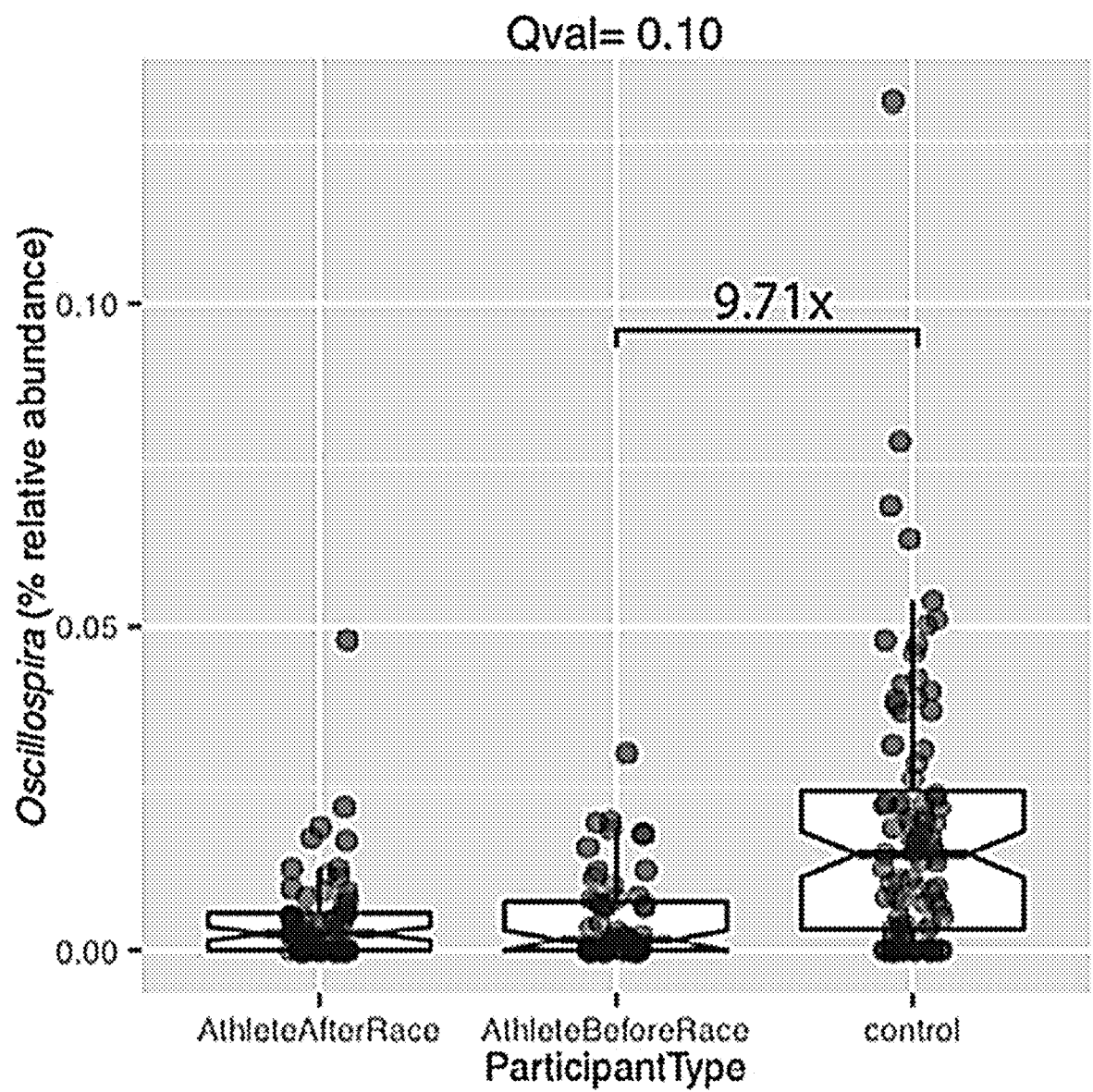
FIG. 2B depicts data demonstrating lower amount of *Oscillospira* in an athlete after a race and before a race compared to a control.

The following bacteria was identified in an athlete as being significantly reduced in abundance after running a marathon: Family: Ruminococcaceae; Genus: *Oscillospira*. Averages of 16S sequences, grouped by study participant type, show a 10 fold increase in *Oscillospira* abundance in controls as compared to athletes before the race (FIG. 2B). This genus has been shown to be negatively correlated with blood lactate levels (lactic acid), with a reduction in genus abundance when blood lactate levels are high. The disclosure provides a method of increasing *Oscillospira* abundance to reduce lactate and improve endurance for extended intense exercise, by preventing lactate buildup.

Example VI

Figure 2C:
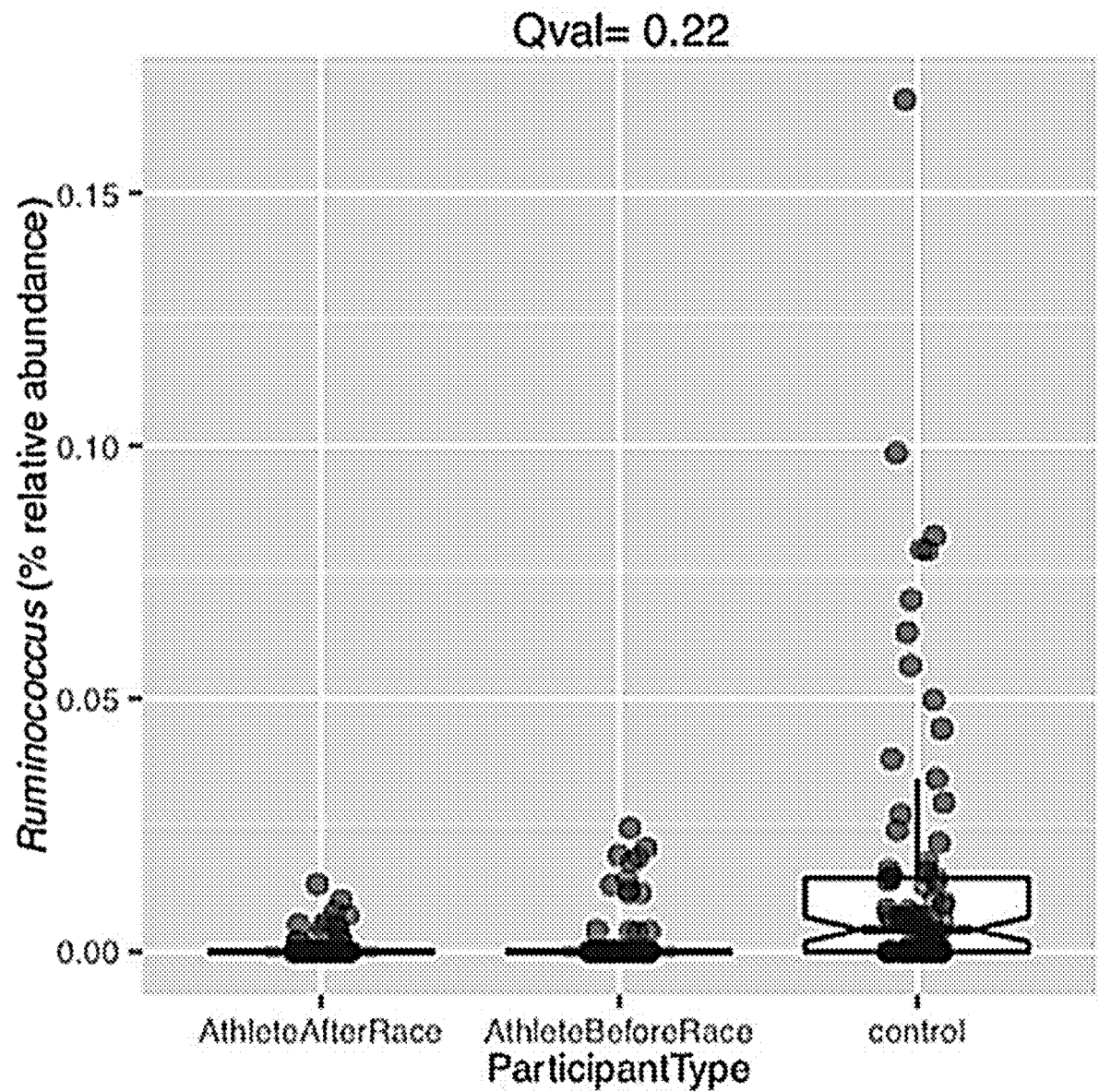
FIG. 2C depicts data demonstrating lower amount of *Ruminococcus* in an athlete after a race compared and before a race compared to a control.

The following bacteria was identified in an athlete as being significantly reduced in abundance after running a marathon: Family: Ruminococcaceae; Genus: *Ruminococcus*. Average of 16S sequences, grouped by study participant type, show the presence of the *Ruminococcus* genus in controls as compared to essentially zero presence in athletes (FIG. 2C). This genus has been shown to be negatively correlated with blood lactate (lactic acid) levels, with a reduction in genus abundance when blood lactate levels are high. The disclosure provides a method of increasing *Ruminococcus* abundance to reduce lactate and improve endurance for extended intense exercise, by preventing lactate buildup.

Example VII

Figure 3A:
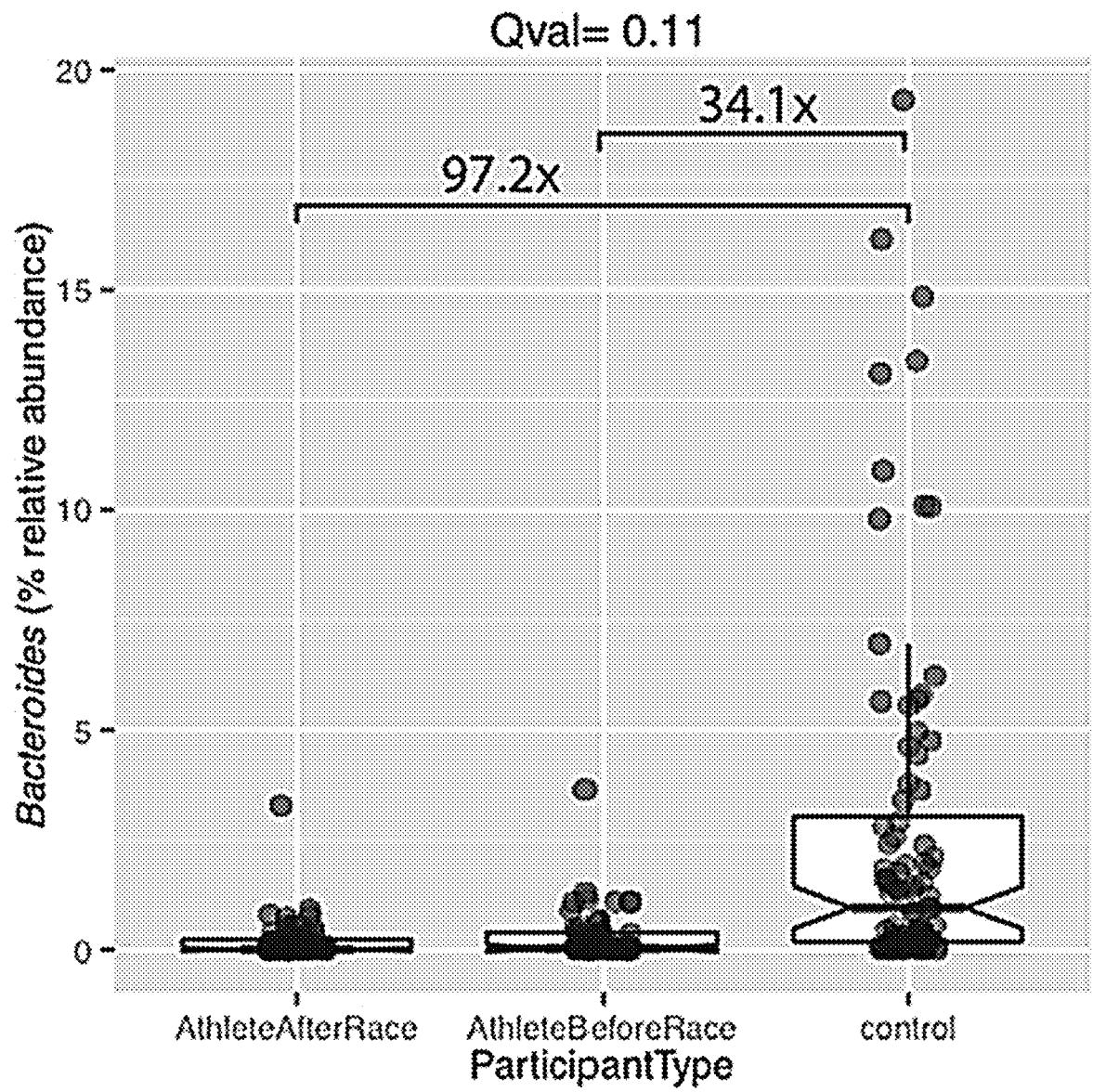
FIG. 3A depicts data demonstrating lower amount *Bacteroides* in an athlete after a race compared and before a race compared to a control.

The following bacteria was identified in an athlete as being significantly reduced in abundance after running a marathon: Family: Bacteroidaceae; Genus: *Bacteroides*. Average of 16S sequences, grouped by study participant type, show a 34 fold and 97 fold increase in controls compared to athletes before and after the marathon, respectively (FIG. 3A). *Bacteroides* abundance has been correlated with health, anti-obesity, and anti-inflammation. The disclosure provides a method of increasing *Bacteroides* abundance in athletes to reduce inflammation and improve recovery and to reduce obesity.

Example VIII

Figure 3B:
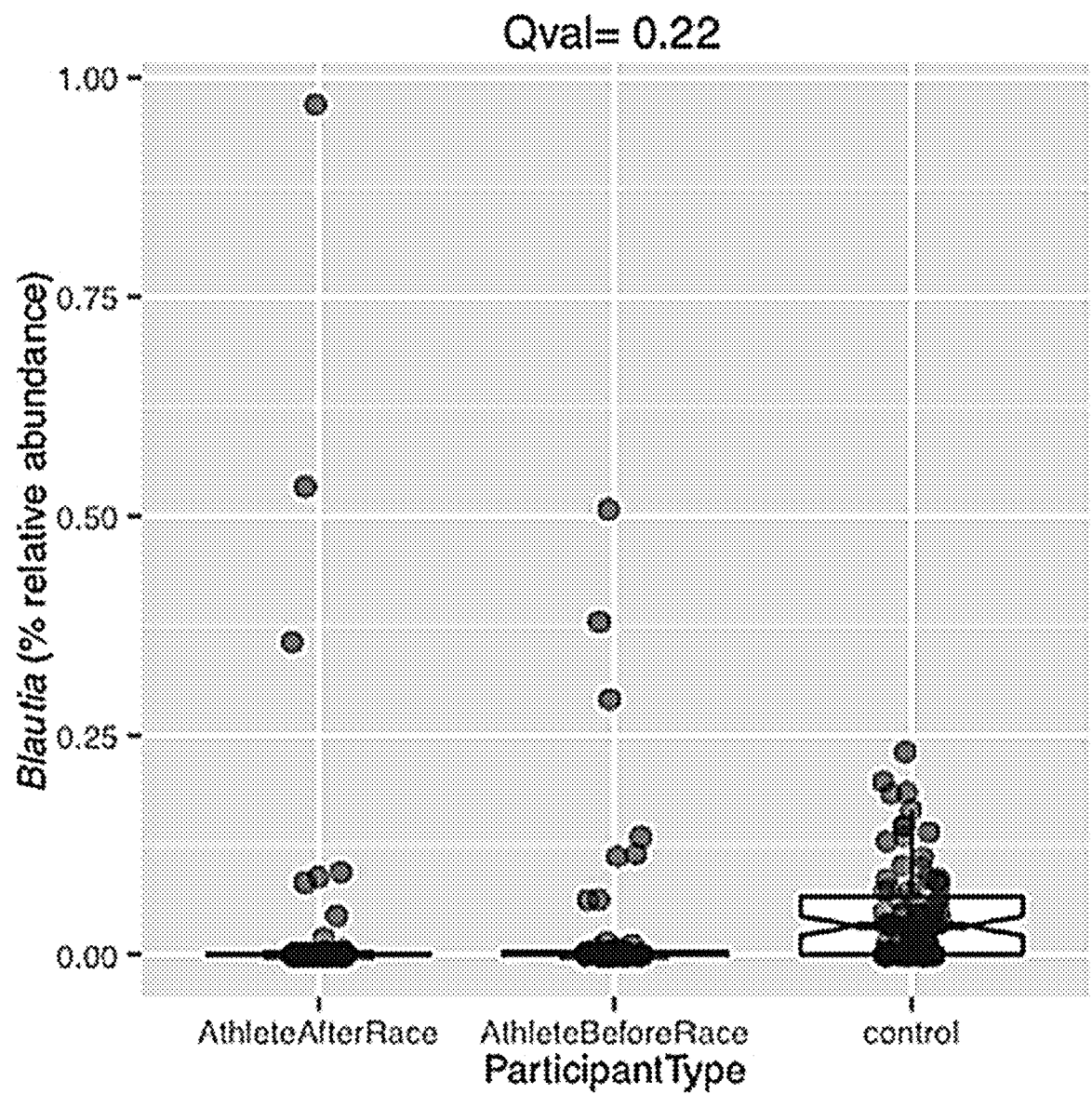
FIG. 3B depicts data demonstrating lower amount of *Blautia* in an athlete compared to a control.

The following bacteria was identified in an athlete as being significantly reduced in abundance after running a marathon: Family: Lachnospiraceae; Genus: *Blautia*. Average of 16S sequences, grouped by study participant type, show the presence of the *Blautia* genus in controls as compared to essentially zero presence in athletes (FIG. 3B). *Blautia* abundance has been associated with anti-inflammation. The disclosure provides a method of increasing *Blautia* abundance in athletes to reduce inflammation and improve recovery.

Example X

Figure 3C:
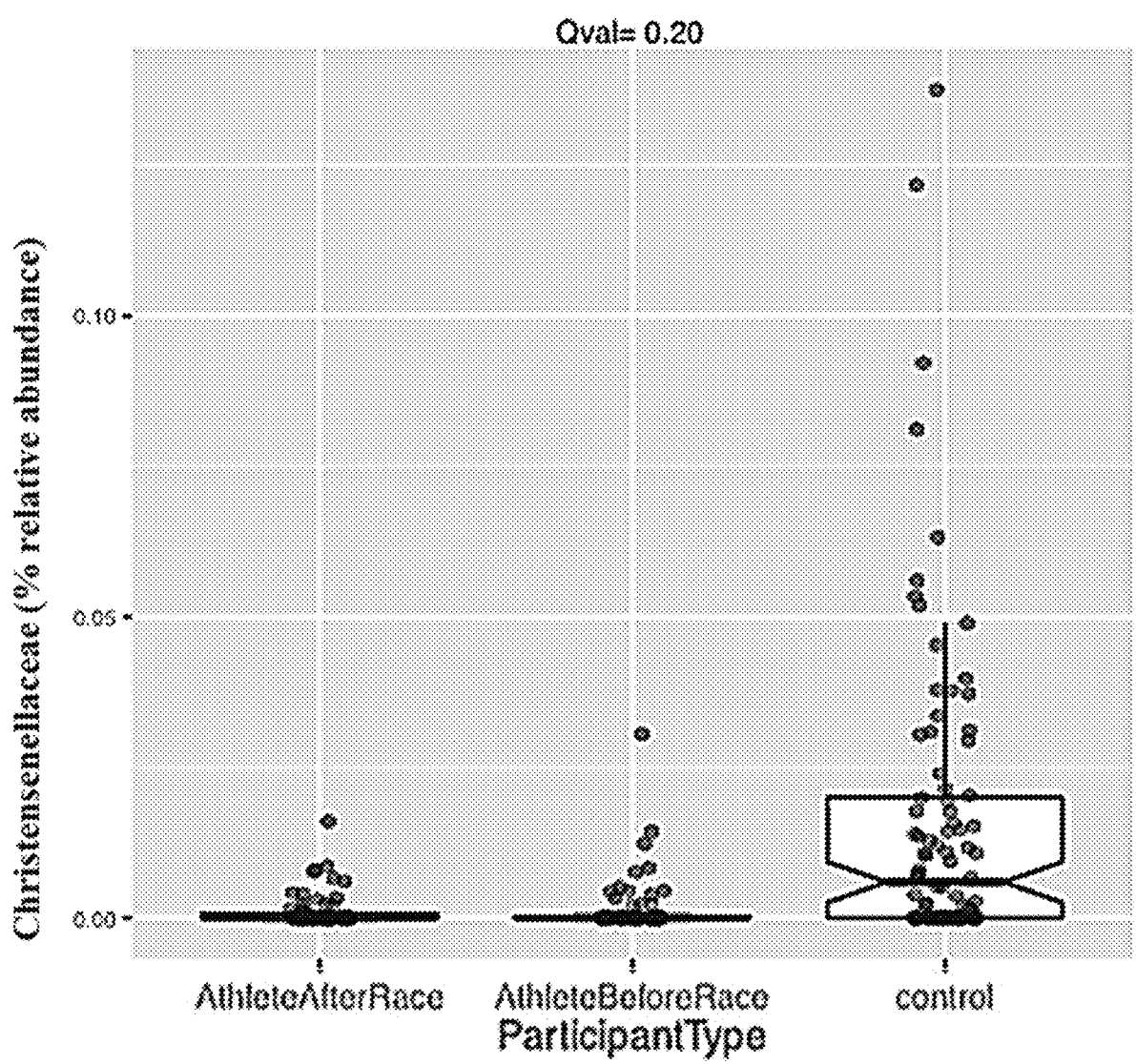
FIG. 3C depicts data demonstrating lower amounts of Christensenellaceae in an athlete after a race and before a race compared to a control.

The following bacteria was identified in an athlete as being significantly reduced in abundance after running a marathon: Family: Christensenellaceae. Average of 16S sequences, grouped by study participant type, show the presence of the Christensenellaceae family in controls as compared to essentially zero presence in athletes (FIG. 3C). Members of this bacterial family have been associated with anti-obesity functions. The disclosure provides a method of increasing Christensenellaceae abundance in individuals to reduce or prevent obesity.

Example XI

Figure 4A:
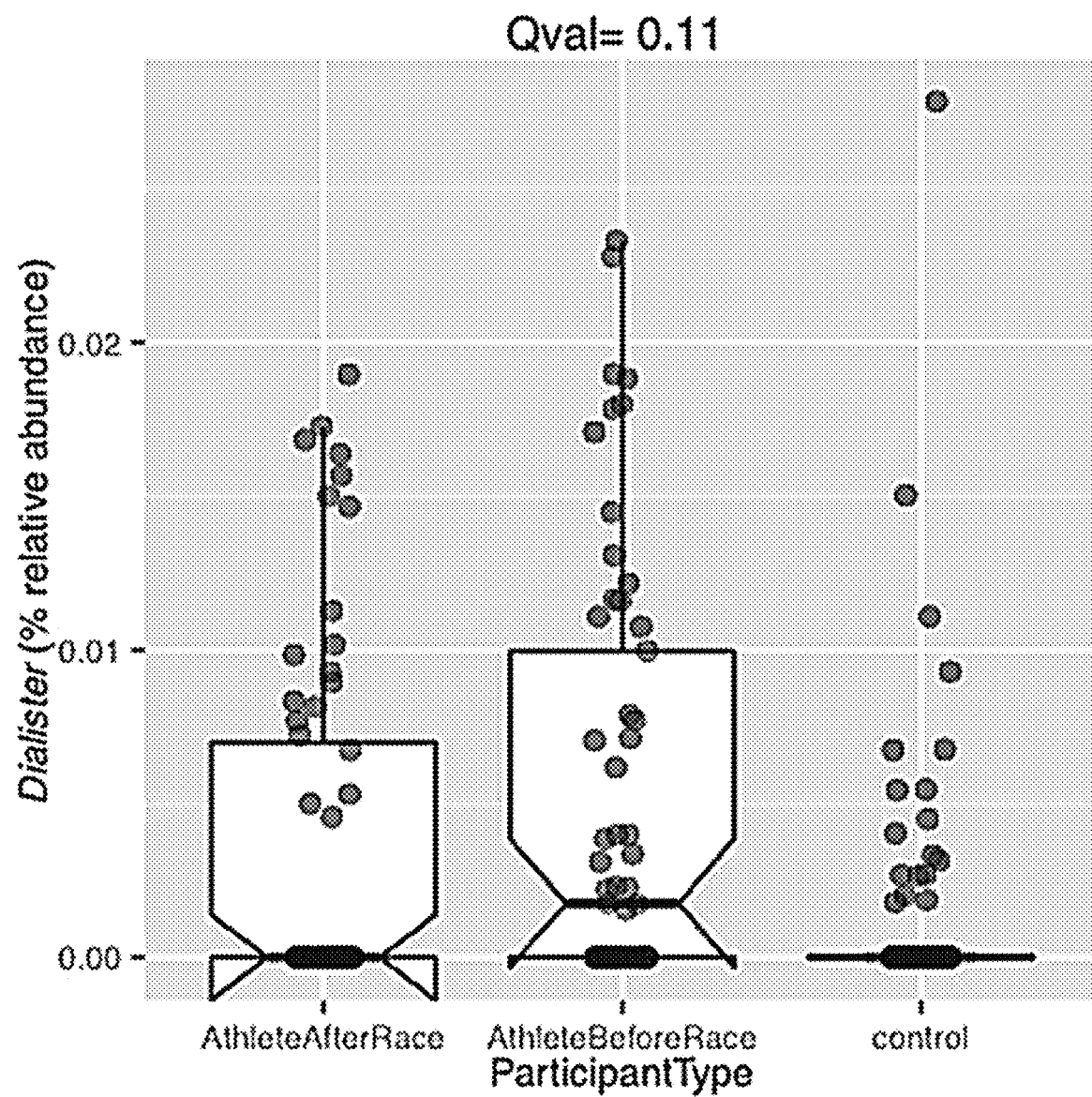
FIG. 4A depicts data demonstrating higher amount of *Dialister* in an athlete compared to a control.

The following bacteria was identified in an athlete as being significantly elevated in abundance after running a marathon: Family: Veillonellaceae; Genus: *Dialister*. Average of 16S sequences, grouped by study participant type show a presence of the *Dialister* genus in athletes as compared to essentially zero presence in controls (FIG. 4A). This genus has been correlated with reductions in levels of the pro-inflammatory cytokine Interleukin-6, so as to provide anti-inflammatory functions. The disclosure provides a method of increasing *Dialister* abundance in athletes to reduce inflammation and improve recovery.

Example XII

Figure 4B:
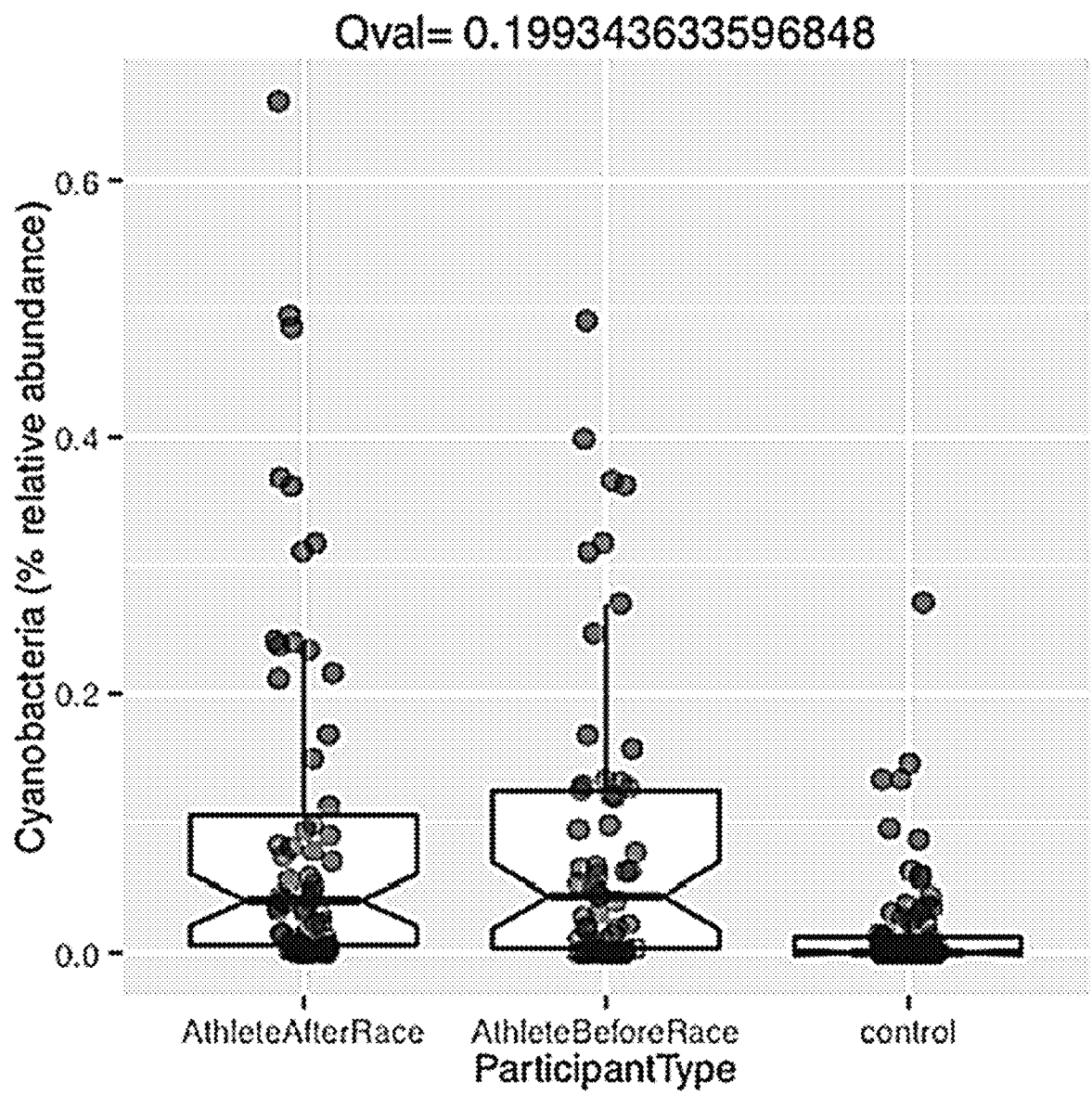
FIG. 4B depicts data demonstrating higher amount of Cyanobacteria in an athlete compared to a control.

The following bacteria was identified in an athlete as being significantly elevated in abundance after running a marathon: Phylum: Cyanobacteria. Average of 16S sequences, grouped by study participant type show a presence of the phylum cyanobacteria in athletes as compared to essentially zero presence in controls (FIG. 4B). Cyanobacteria produce vitamins and ferment carbohydrates in the gut for energy production. A higher abundance of cyanobacteria in athletes indicates higher energy demands. The disclosure provides a method of increasing Cyanobacteria abundance in athletes to improve energy metabolism and performance.

Example XIII

The disclosure provides administering one or more bacteria from genus *Veillonella*, genus *Faecalibacterium*, genus *Phascolarctobacteria*, genus *Oscillospira*, genus *Ruminococcus*, genus *Bacteroides*, genus *Blautia*, family Christensenellaceae, genus *Dialister*, and phylum cyanobacteria. The bacteria of the above examples found to be altered in abundance between participant types is summarized in FIG. 5.

Example XIV

Figure 6A:
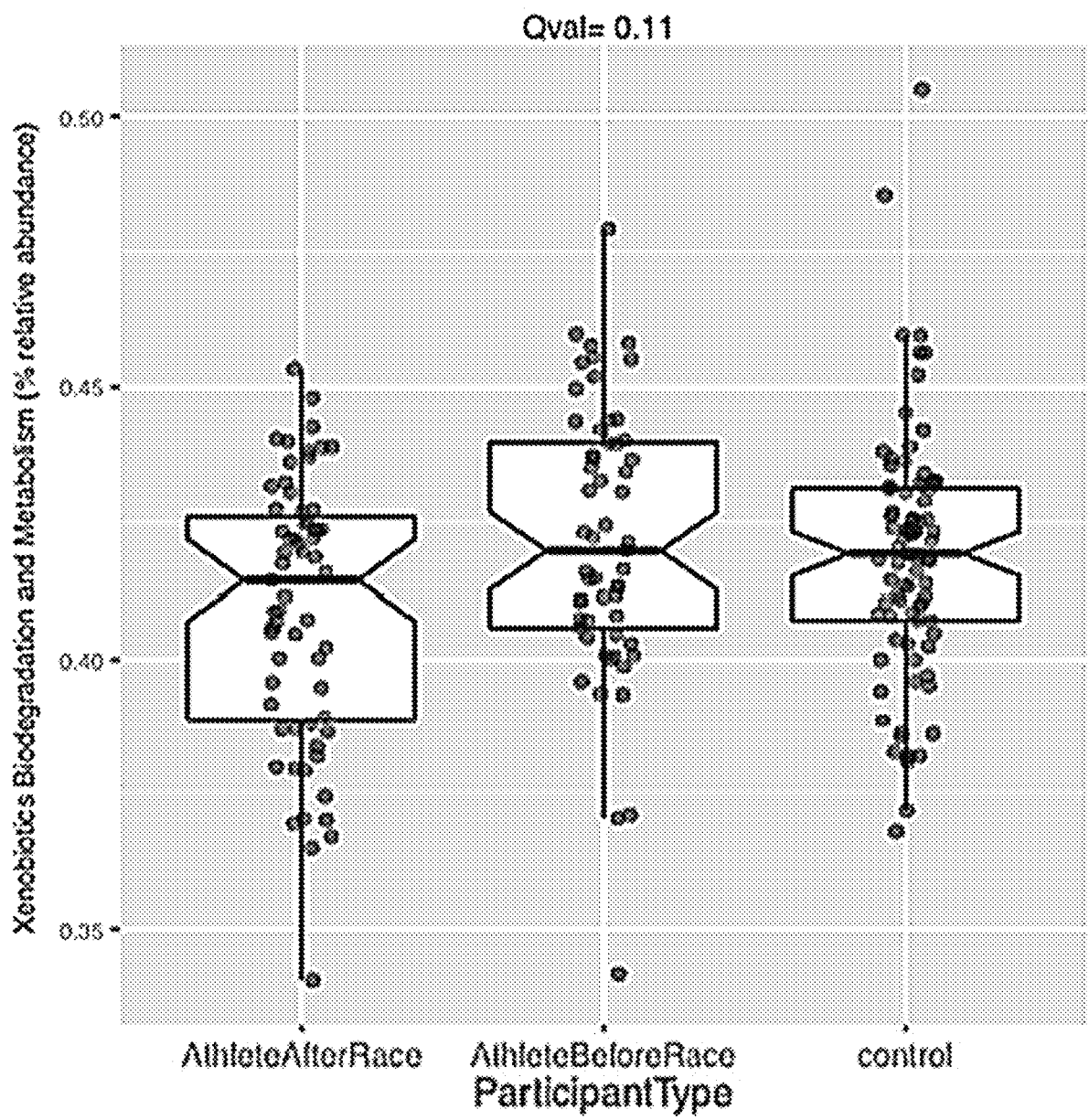
FIG. 6A is depicts data demonstrating reduction in bacteria participating in the xenobiotic metabolism pathway.

The disclosure provides administering one or more bacteria for xenobiotics biodegradation and metabolism. This pathway pertains to the degradation of harmful chemicals, drugs, pollutants, and toxins. The disclosure provides that a reduction in this pathway (see FIG. 6A) renders athletes, after running a marathon (or other intense physical exertion) more susceptible to harmful agents in the body (some which may be a results of cellular inflammation). The disclosure provides a method of restoring the xenobiotic metabolism pathway, by increasing the abundance of bacterial species which promote it, to promote recovery and overall health in athletes.

Figure 6B:
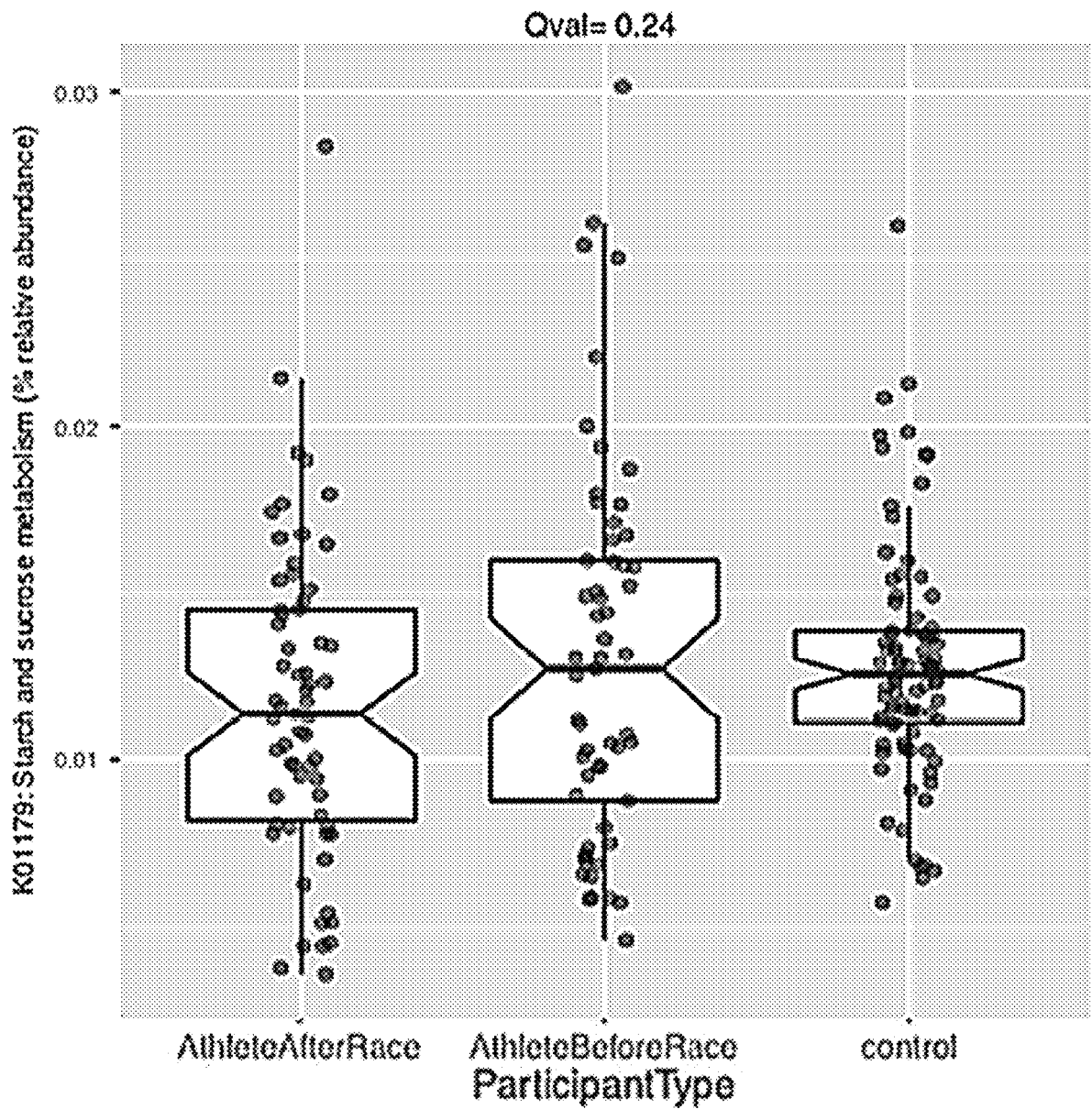
FIG. 6B depicts data demonstrating reduction in bacteria participating in the starch and sucrose metabolism pathway.

The disclosure provides administering one or more bacteria for starch and sucrose metabolism. This pathway pertains to the breakdown of carbohydrates, which many runners are known to load up on as a source of energy before a race. The disclosure provides that a reduction in this pathway (FIG. 6B) renders athletes, after running a marathon (or other intense physical exertion) depleted of bacteria that aid in energy harvest from carbohydrates. The disclosure provides a method of restoring the starch and sucrose metabolism pathway, by increasing the abundance of bacterial species which promote it, to promote endurance in athletes by enabling longer and more efficient energy extraction from food.

Example XV

The disclosure provides a method of enriching and/or isolating a lactic acid fermenting bacterial species. A biological sample, such as a fecal sample, is contacted to a substrate including lactate (lactic acid) and the biological sample is incubated for a period of time and at a desired temperature sufficient for growth of any lactic acid consuming bacterial species. Lactic acid consuming bacterial species may then be isolated for further processing or testing or harvested or purified for use as a probiotic supplement using methods known to those of skill in the art. The incubated sample may be analyzed for presence of lactic acid consuming bacterial species, such as sequencing using next generation sequencing methods as are known in the art.

A particular exemplary lactic acid consuming bacterial species is *Veillonella* as described herein. According to one aspect, *Veillonella* is enriched within and isolated from a fecal sample. Fecal samples collected from athletes were resuspended into 2 ml of Phosphate Buffered Saline and vortexed to homogenize. Serial dilutions of resuspended samples were made and then seeded onto lactate agar plates, which per liter, includes: 5 g yeast extract, 0.75 g sodium thioglycolate, 0.002 g of Gram Basic Fuchsin, 21 ml of 60% sodium lactate, and 15 g of agar. Lactate agar was adjusted to a pH of 7.5 before autoclaving and supplemented with 7.5 ug/ml of vancomycin after autoclaving. Lactate plates seeded with diluted fecal samples were grown at 37° C. under anaerobic conditions for 48-96 h, at which time individual colonies were picked for sequencing and glycerol storage. For determining efficiency of *Veillonella* enrichment, lactate plates seeded with diluted fecal samples were harvested for DNA after 48-96 h of growth and processed for next-generation sequencing to access percentage of bacterial isolates identified as *Veillonella*, and compared to original fecal samples.

Figure 7:
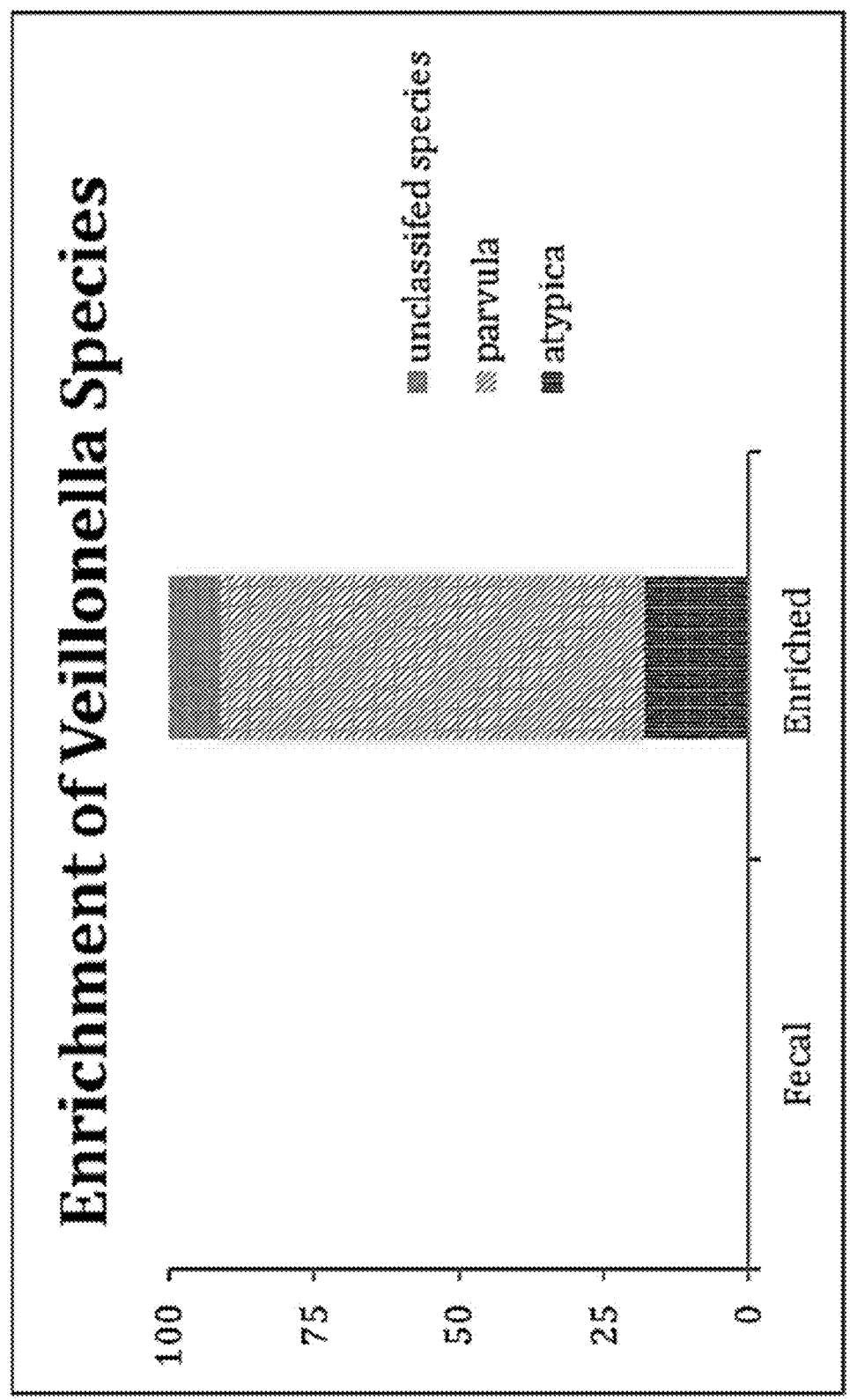
FIG. 7 depicts data of bacterial enrichment when incubated on a lactate agar plate.

FIG. 7 depicts results of the process showing enrichment of lactic acid fermenting *Veillonella* species from athlete fecal samples. While the *Veillonella* species are typically present at less than 1 percent in fecal microbial communities, growth on lactate agar results in enrichment and can result in up to 100 percent enrichment, including the individual species: *Veillonella atypical*, *Veillonella parvula*, as well as unclassified species of the *Veillonella* genus. In this manner, numerous *Veillonella* species can be purified from athlete gut microbiomes and then tested for efficacy, as a probiotic supplement or included in a probiotic formulation, in reducing lactic acid levels in athletes to prevent fatigue and soreness, and promote endurance.

The invention claimed is:

1. A probiotic composition formulated for administration to a human, comprising: at least $10^5$ CFU of bacteria of the genus *Veillonella*, wherein the bacteria are in a dried form.

2. The probiotic composition of claim 1, wherein the probiotic composition further comprises one or more bacteria selected from the group consisting of: *Faecalibacterium*, *Phascolarctobacteria*, *Oscillospira*, *Ruminococcus*, *Bacteroides*, *Blautia*, *Christensenellaceae*, *Dialister*, *Lactobacillus*, and *Cyanobacteria*.

3. The probiotic composition of claim 1, wherein the probiotic composition comprises *Veillonella atypica*.

4. The probiotic composition of claim 1, wherein the probiotic composition comprises *Veillonella parvula*.

5. The probiotic composition of claim 1, wherein the probiotic composition comprises *Veillonella parvula* and *Veillonella atypica*.

6. The probiotic composition of claim 1, wherein the probiotic composition further comprises one or more *Lactobacillus* bacteria.

7. The probiotic composition of claim 1, wherein the *Veillonella* bacteria are live bacteria.

8. The probiotic composition of claim 1, wherein the probiotic composition further comprises one or more prebiotics, minerals, vitamins, amino acids, or any combination thereof.

9. The probiotic composition of claim 1, wherein the probiotic composition further comprises one or more nutraceutical compounds.

10. The probiotic composition of claim 1, wherein the probiotic composition further comprises one or more flavoring agents.

11. The probiotic composition of claim 1, wherein the probiotic composition is formulated for oral delivery.

12. The probiotic composition of claim 1, wherein the probiotic composition is encapsulated.

13. The probiotic composition of claim 1, wherein the probiotic composition is a dietary supplement.

14. The probiotic composition of claim 1, wherein the probiotic composition is a dietary supplement formulated to improve athletic training, performance, and/or recovery.

15. The probiotic composition of claim 1, wherein the probiotic composition is formulated as an ingestible liquid medium, a gel medium, a food stuff, a food product, a beverage, a freeze dried product, a powder, a yogurt, a capsule, a tablet, a pill, a gelatin capsule, a caplet, a chewable formulation, or a dissolvable formulation.

16. The probiotic composition of claim 1, wherein the probiotic composition is formulated as a food product or food stuff.

17. The probiotic composition of claim 1, wherein the probiotic composition is formulated as a food product or food stuff, which further comprises prebiotics, minerals, vitamins, amino acids, proteins, or any combination thereof.

18. The probiotic composition of claim 1, wherein the probiotic composition is formulated as a powder food stuff.

19. The probiotic composition of claim 1, wherein the probiotic composition is formulated as a powder food stuff, which further comprises prebiotics, minerals, vitamins, amino acids, proteins, or any combination thereof.

20. The probiotic composition of claim 1, wherein the probiotic composition is formulated as a yogurt.

21. The probiotic composition of claim 1, wherein the probiotic composition is formulated as a yogurt and the yogurt is a yogurt drink or a yogurt-based beverage.

22. The probiotic composition of claim 1, wherein the probiotic composition is formulated as a beverage.

23. The probiotic composition of claim 1, wherein the probiotic composition is formulated as a beverage, which further comprises one or more prebiotics, minerals, vitamins, amino acids, proteins, or any combination thereof.

24. The probiotic composition of claim 1, wherein administration of the probiotic composition to a human increases the population of *Veillonella* bacteria within the human.

25. The probiotic composition of claim 1, wherein administration of the probiotic composition to a human increases or maintains training endurance or performance endurance of the human during physical exercise.

26. The probiotic composition of claim 1, wherein administration of the probiotic composition to a human reduces muscle fatigue of the human during or following physical exercise.

27. The probiotic composition of claim 1, wherein administration of the probiotic composition to a human reduces lactate levels of the human during or following physical exercise.

28. The probiotic composition of claim 1, wherein administration of the probiotic composition to a human reduces inflammation of the human during or following physical exercise.

29. The probiotic composition of claim 1, wherein administration of the probiotic composition to a human increases energy metabolism and/or promotes weight loss of the human.

30. A kit, comprising: the probiotic composition of claim 1 and instructions for administration of the probiotic composition to the human.

31. The probiotic composition of claim 1, wherein the *Veillonella* bacteria are dead bacteria.

32. The probiotic composition of claim 1, wherein the *Veillonella* bacteria are freeze dried *Veillonella* bacteria, spray dried *Veillonella* bacteria, or fluidized bed dried *Veillonella* bacteria.

33. The probiotic composition of claim 32, wherein the *Veillonella* bacteria are freeze dried *Veillonella* bacteria.

\* \* \* \* \*